US012625150B2

United States Patent

(12) United States Patent
Moraitis et al.

(10) Patent No.: US 12,625,150 B2
(45) Date of Patent: May 12, 2026

(54) TREATMENT OF, AND DIFFERENTIAL DIAGNOSIS BETWEEN, ACTH-DEPENDENT CUSHING'S SYNDROME AND ACTH-INDEPENDENT CUSHING'S SYNDROME

(71) Applicant: Corcept Therapeutics Incorporated, Menlo Park, CA (US)

(72) Inventors: Andreas G. Moraitis, Sunny Isles Beach, FL (US); Joseph Belanoff, Woodside, CA (US)

(73) Assignee: Corcept Therapeutics Incorporated, Redwood City, CA (US)

( * ) Notice: Subject to any disclaimer, the term of this patent is extended or adjusted under 35 U.S.C. 154(b) by 849 days.

(21) Appl. No.: 17/786,146

(22) PCT Filed: Dec. 18, 2020

(86) PCT No.: PCT/US2020/065916

§ 371 (c)(1),
(2) Date: Jun. 16, 2022

(87) PCT Pub. No.: WO2021/127376

PCT Pub. Date: Jun. 24, 2021

(65) Prior Publication Data

US 2023/0358768 A1 Nov. 9, 2023

Related U.S. Application Data

(60) Provisional application No. 62/952,242, filed on Dec. 21, 2019.

(51) Int. Cl.
*G01N 33/74* (2006.01)
*A61K 31/567* (2006.01)

(52) U.S. Cl.
CPC ........... *G01N 33/74* (2013.01); *A61K 31/567* (2013.01); *G01N 2333/695* (2013.01); *G01N 2800/04* (2013.01)

(58) Field of Classification Search
CPC ................ G01N 33/74; G01N 33/743; G01N 2333/695; G01N 2333/723; G01N 2800/04; A61K 31/567; A61K 31/4738; A61K 31/513; A61P 5/38; Y10T 436/20; Y10T 436/200833; Y10T 436/203332
USPC ............................ 436/86, 87, 127, 128, 131
See application file for complete search history.

(56) References Cited

U.S. PATENT DOCUMENTS

| | | | | |
|---|---|---|---|---|
| 4,386,085 A | | 5/1983 | Teutsch et al. | |
| 8,685,973 B2 | | 4/2014 | Clark et al. | |
| 9,829,495 B2 | * | 11/2017 | Moraitis | A61K 31/4745 |
| 10,610,534 B2 | * | 4/2020 | Moraitis | A61P 43/00 |
| 2010/0261693 A1 | * | 10/2010 | Ulmann | A61K 31/567 514/179 |
| 2014/0170768 A1 | * | 6/2014 | Ehrenkranz | G01N 33/74 436/501 |
| 2018/0011113 A1 | * | 1/2018 | Moraitis | G01N 33/74 |
| 2018/0125856 A1 | * | 5/2018 | Moraitis | A61P 35/00 |

FOREIGN PATENT DOCUMENTS

| | | |
|---|---|---|
| WO | 2013177559 | 11/2013 |
| WO | 2015077530 | 5/2015 |
| WO | 2016140867 A1 | 9/2016 |
| WO | 2017027851 | 2/2017 |
| WO | 2017127448 | 7/2017 |

OTHER PUBLICATIONS

European Patent Application No. 20902331.6 , "Extended European Search Report", Oct. 25, 2023, 7 pages.

International Patent Application No. PCT/US2020/065916 , "International Preliminary Report on Patentability", Jun. 30, 2022, 6 pages.

Clark et al., "1H-Pyrazolo[3,4-g]Hexahydro-Isoquinolines as Selective Glucocorticoid Receptor Antagonists with High Functional Activity", Bioorganic & Medicinal Chemistry Letters, vol. 18, No. 4, Feb. 15, 2008, pp. 1312-1317.

International Patent Application No. PCT/US2020/065916 , International Search Report and the Written Opinion, Mailed on Apr. 15, 2021, 14 pages.

* cited by examiner

*Primary Examiner* — Maureen Wallenhorst
(74) *Attorney, Agent, or Firm* — Kilpatrick Townsend & Stockton LLP

(57) ABSTRACT

Methods for treating and differential diagnosis between ACTH-Dependent and ACTH-Independent Cushing's syndrome are disclosed, in which a glucocorticoid receptor antagonist (GRA) is administered to a Cushing's syndrome patient with a basal ACTH level less than about 25 pg/mL. If i) the patients blood ACTH and ii) the patients blood cortisol, or adrenal hormone, or adrenal pre-hormone levels rise, or if the ACTH:cortisol ratio increases, then ACTH-Dependent Cushing's syndrome is diagnosed. If those levels do not rise, or if the ACTH:cortisol ratio decreases, then ACTH-Independent Cushing's syndrome is diagnosed. In some instances, the patient is recovering from surgery to remove an ACTH secreting tumor, and the method described herein is used to determine if the tumor resection was successful or complete. The GRA may be mifepristone, or a non-steroidal GRA having a heteroaryl-ketone fused azadecalin backbone, an octahydro fused azadecalin backbone, a cyclohexyl pyrimidine backbone, or a fused azadecalin backbone.

16 Claims, No Drawings

TREATMENT OF, AND DIFFERENTIAL DIAGNOSIS BETWEEN, ACTH-DEPENDENT CUSHING'S SYNDROME AND ACTH-INDEPENDENT CUSHING'S SYNDROME

CROSS-REFERENCE TO RELATED APPLICATIONS

This application is a 371 U.S. National Phase of PCT International Patent Application No. PCT/US2020/065916, filed Dec. 18, 2020, which claims priority to, and the benefit of, U.S. Provisional Patent Application Ser. No. 62/952,242, filed Dec. 21, 2019, the entire contents of which are hereby incorporated by reference in their entirety.

BACKGROUND

Cortisol is a steroid produced by the adrenal glands. Cortisol is used in the body to respond to physical and emotional stress, and maintain adequate energy supply and blood sugar levels. Cortisol production is highly regulated by the hypothalamic-pituitary-adrenal axis (HPA) through a complex set of direct influences and negative feedback interactions. In healthy individuals, insufficient cortisol in the bloodstream triggers the hypothalamus to release corticotropin-releasing hormone (CRH) which signals to the pituitary gland to release adrenocorticotropic hormone (ACTH), which in turn stimulates the adrenal glands to produce more cortisol. ACTH also stimulates the production and secretion of adrenal pre-hormones and other adrenal hormones (e.g., 17α-hydroxy pregnenolone, 17α-hydroxy progesterone, 11-deoxycortisol, pregnenolone, progesterone, 11-deoxycorticosterone, corticosterone, 18-hydroxycorticosterone, aldosterone, dehydroepiandrosterone (androstenolone, DHEA), dehydroepiandrosterone sulfate (DHEA-S), and androstenedione). Excessive cortisol inhibits the hypothalamus from producing CRH, thus inhibiting the pituitary gland from releasing ACTH, which in turn suppresses cortisol production (and also reduces production of other adrenal pre-hormones and adrenal hormones). The HPA regulation also results in a diurnal rhythm of cortisol levels, reaching peaks in the morning and nadirs around midnight. Pathological conditions associated with the HPA can affect the diurnal rhythm of the cortisol and ACTH production and cause serious health problems. Impairment of the hypothalamic-pituitary-adrenal (HPA) axis due to a pituitary dysfunction disorder or an adrenal dysfunction disorder, such as adrenal insufficiency can cause deficient production or secretion of cortisol, or disorders which result in excess cortisol such as Cushing's syndrome (which may result, e.g., from hormone-secreting tumors, or administration of drugs which mimic cortisol).

The biological effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) J. Clin. Endocrinol. Metab. 59:25). Mifepristone binds to the GR with high affinity, with a dissociation constant (Kd) of 10-9 M (Cadepond (1997) Annu. Rev. Med. 48:129).

Hypercortisolism, often referred to as Cushing's syndrome, is caused by excessive activity of the stress hormone cortisol. Endogenous Cushing's syndrome is an orphan disease that most often affects adults aged 20-50. In the United States, an estimated 20,000 patients have Cushing's syndrome, with about 3,000 new patients being diagnosed each year. Symptoms vary, but most people experience one or more of the following manifestations: high blood sugar (hyperglycemia), diabetes, high blood pressure, upper-body obesity, rounded face, increased fat around the neck, thinning arms and legs, easy bruising, facial plethora, acne, red purple stripes across the body, severe fatigue and weak muscles. Irritability, anxiety, cognitive disturbances and depression are also common. Cushing's syndrome can affect every organ system in the body and can be lethal if not treated effectively.

Cushing's syndrome includes ACTH-independent Cushing's syndrome, characterized by an overproduction of cortisol in the absence of elevation of ACTH secretion; and ACTH-dependent Cushing's syndrome, characterized by excessive ACTH secretion.

ACTH-Dependent Cushing's syndrome includes roughly 70% of patients having endogenous Cushing's syndrome and consists of two major forms: Cushing Disease and ectopic ACTH syndrome. The former is caused by a pituitary tumor and the latter is caused by a tumor outside the pituitary. Correct differential diagnosis between ACTH-Dependent Cushing's syndrome on the one hand, and ACTH-Independent Cushing's syndrome on the other hand, is important for endocrinologists to recommend transsphenoidal surgery (for a pituitary tumor), adrenal surgery, or appropriate imaging to localize and identify the source of the ectopic ACTH secretion.

Cushing's syndrome patients may be treated by glucocorticoid receptor modulators, such as mifepristone, to reduce or block the effects of excess cortisol (see, e.g., U.S. Pat. Nos. 9,943,526; 9,956,216, both of which patents are hereby incorporated by reference in their entireties). Cushing's syndrome patients may be treated surgically to remove, as much as possible, the cause or source of the excess cortisol, and by other means. However, it may be critical to identify, or to localize, the cause or source of excess cortisol. Accordingly, methods for identifying those Cushing's syndrome patients who suffer from ACTH-Dependent Cushing's syndrome who are in need of transsphenoidal surgery, or for whom transsphenoidal was incompletely successful or was unsuccessful; those Cushing's syndrome patients who suffer from ACTH-Dependent Cushing's syndrome who are in need of surgery for an ectopic tumor; and for identifying those Cushing's syndrome patients who suffer from ACTH-Independent Cushing's syndrome are needed.

SUMMARY

Provided herein are methods for treating a Cushing's syndrome patient while determining whether the patient suffers from ACTH-Dependent Cushing's syndrome, or whether the patient suffers from ACTH-Independent Cushing's syndrome. In embodiments, the treatment of Cushing's syndrome comprises administration of a glucocorticoid receptor modulator (GRM). In embodiments, the treatment of Cushing's syndrome comprises administration of a glucocorticoid receptor antagonist (GRA). In some embodiments, the GRA is a selective inhibitor of the glucocorticoid receptor. In embodiments, the GRA is mifepristone. In some embodiments, the GRA is administered orally.

The methods disclosed herein include selecting a patient with Cushing's syndrome having a basal plasma or serum cortisol level, and having a detectable basal plasma or serum ACTH level that is less than about 25 picograms per milliliter (pg/mL); administering a GRA to said patient; and, a) if the patient's plasma or serum ACTH and/or cortisol levels rise above their respective basal levels after GRA administration, determining that the patient has ACTH-Dependent Cushing's syndrome; or b) if neither the patient's plasma or serum ACTH nor the patient's cortisol levels rise after GRA administration, determining that the patient has ACTH-Independent Cushing's syndrome. In embodiments of the methods disclosed herein, if the patient's plasma or serum ACTH rise above 25 pg/mL after GRA administration, then the patient is determined to have ACTH-Dependent Cushing's syndrome.

In embodiments, the methods include transsphenoidal surgery to remove pituitary tumor tissue in patients identified as having ACTH-Dependent Cushing's syndrome. In embodiments, the methods include surgery for the removal or resection of an ectopic tumor for patients identified as having ectopic ACTH-Dependent Cushing's syndrome. In embodiments, the methods include adrenal surgery for ACTH-Independent Cushing's patients identified as having an adrenal tumor causing adrenal Cushing's syndrome.

In embodiments, in addition to or in place of measuring cortisol, the methods include measuring other adrenal hormones, or measuring adrenal pre-hormones, or measuring both other adrenal hormones and adrenal pre-hormones. Thus, the methods disclosed herein include selecting a patient with Cushing's syndrome having i) a basal plasma or serum adrenal hormone level, ii) a basal plasma or serum adrenal pre-hormone level, or both i) and ii); and having a detectable basal plasma or serum ACTH level that is less than about 25 pg/mL, e.g., between about 5 to 25 pg/mL; administering a glucocorticoid receptor antagonist (GRA) to said patient; and, a) if the patient's plasma or serum ACTH and/or adrenal hormone or adrenal pre-hormone levels rise above their respective basal levels after GRA administration, determining that the patient has ACTH-Dependent Cushing's syndrome; or b) if neither the patient's plasma or serum ACTH nor the patient's adrenal hormone or levels rise after GRA administration, determining that the patient has ACTH-Independent Cushing's syndrome. In embodiments, the adrenal pre-hormone or adrenal hormone is selected from 17α-hydroxy pregnenolone, 17α-hydroxy progesterone, 11-deoxycortisol, pregnenolone, progesterone, 11-deoxycorticosterone, corticosterone, 18-hydroxycorticosterone, aldosterone, dehydroepiandrosterone (androstenolone, DHEA), dehydroepiandrosterone sulfate (DHEA-S), and androstenedione. In embodiments of the methods disclosed herein which include measuring other adrenal hormones or measuring adrenal pre-hormones, the basal plasma or serum ACTH level for selecting a patient with Cushing's syndrome that is less than about 25 pg/mL is between about 5 to about 20 pg/mL. In embodiments of the methods disclosed herein which include measuring other adrenal hormones or measuring adrenal pre-hormones, the basal plasma or serum ACTH level for selecting a patient with Cushing's syndrome that is less than about 25 pg/mL is between about 5 to about 15 pg/mL. In embodiments of the methods disclosed herein which include measuring other adrenal hormones or measuring adrenal pre-hormones, the basal plasma or serum ACTH level for selecting a patient with Cushing's syndrome that is less than about 25 pg/mL is between about 5 to about 10 pg/mL. In embodiments of the methods disclosed herein which include measuring other adrenal hormones or measuring adrenal pre-hormones, the patient has a basal plasma or serum cortisol level, and plasma or serum cortisol is measured after GRA administration; after GRA administration, a rise in cortisol levels above the basal levels indicates that the patient has ACTH-Dependent Cushing's syndrome; orb) lack of such a rise in the patient's plasma or serum cortisol levels, combined with a lack of a rise in the patient's ACTH levels rise after GRA administration, indicates that the patient has ACTH-Independent Cushing's syndrome. In embodiments, the patient is recovering from surgery to remove an ACTH secreting tumor, and the method described herein is used to determine if the tumor resection was successful or complete.

A patient suffering from ACTH-Dependent Cushing's syndrome may have, e.g., an ACTH-secreting pituitary tumor. The ACTH secreting tumor can be a pituitary ACTH secreting tumor. In other cases of ACTH-Dependent Cushing's syndrome, the ACTH secreting tumor is an ectopic ACTH secreting tumor. In some instances, the patient is recovering from surgery to remove an ACTH secreting tumor, and the method described herein is used to determine if the tumor resection was successful or complete. A patient suffering from ACTH-Independent Cushing's syndrome may suffer from adrenal Cushing's syndrome (i.e., may have an adrenal tumor).

In embodiments, the methods include steps of measuring, in a sample obtained from the patient, a basal plasma or serum cortisol level, and of measuring a basal plasma or serum ACTH level. In embodiments, the methods include steps of measuring, in a sample obtained from the patient, a basal plasma or serum adrenal hormone or adrenal pre-hormone level, and of measuring a basal plasma or serum ACTH level. In some embodiments, the sample obtained from the patient is a plasma, serum, saliva or urine sample. In some embodiments, step (a) of the method includes measuring the basal (morning) level of total cortisol (e.g., plasma total cortisol, serum total cortisol or salivary total cortisol) or free cortisol (e.g., plasma free cortisol, serum free cortisol, or urine free cortisol) in a sample obtained from the patient prior to performing step (b).

In embodiments, the methods comprise determining a ratio between the ACTH level and the cortisol level, termed an ACTH:cortisol ratio. An ACTH:cortisol ratio is calculated by dividing the numerical value of the ACTH level (e.g., the plasma or serum ACTH level) by the numerical value of the cortisol level (e.g., the plasma or serum cortisol level). If the ACTH:cortisol ratio decreases after GRA administration, then the patient is diagnosed with ACTH-independent Cushing's syndrome. If the ACTH:cortisol ratio increases after GRA administration, then the patient is diagnosed with ACTH-dependent Cushing's syndrome.

Cushing's syndrome is a disease of hypercortisolism, and may be treated by administration of a GRA, and hyperglycemia secondary to hypercortisolism may be treated by administration of a GRA. For example, as is known in the art, Cushing's syndrome may be treated by administration of mifepristone, and hyperglycemia secondary to hypercortisolism may be treated by administration of mifepristone.

In some cases, the GRA is a selective inhibitor of the glucocorticoid receptor (GR). In embodiments, the GRA is mifepristone. In some embodiments, the GRA comprises a steroidal backbone.

In some embodiments, the GRA has a non-steroidal backbone. In some cases, the GRA backbone is a cyclohexyl pyrimidine. In some cases, the GRA backbone is a fused azadecalin. In some cases, the GRA backbone is a heteroaryl-ketone fused azadecalin. In some cases, the GRA backbone is an octahydro fused azadecalin. Such non-steroidal GRM and GRA compounds are disclosed, for example, in U.S. Pat. Nos. 7,928,237; 8,461,172; 8,685,973; 9,943,526; 9,956,216; 8,859,774; 9,273,047; 9,707,223; 9,943,505; 9,956,216; 10,047,082; and others. All patents, patent application publications, international patents and patent publications, and references cited herein are hereby incorporated by reference in their entireties.

In embodiments, the methods disclosed herein include steps of measuring the level or activity of adrenocorticotropic hormone (ACTH) in a sample from the patient before administering the GRA, and of measuring the level of ACTH in a sample from the patient after administering the GRA to determine whether or not there has been an increase in the level of ACTH. In embodiments, the sample is a blood sample. In some cases, the step of measuring the level of ACTH comprises performing a radioimmunoassay, an immunofluorometric enzyme assay, an enzyme-linked immunosorbent assay, a competitive protein-binding assay, liquid chromatography, or mass spectrometry. In some embodiments, the sample used for measuring the level of ACTH is a plasma or serum sample. A determination that the level of ACTH has risen following GRA administration, whether or not accompanied by a rise in cortisol following GRA administration, indicates that the patient has ACTH dependent Cushing's syndrome. A determination that the level of ACTH has not risen following GRA administration, whether or not accompanied by a failure of cortisol to rise following GRA administration, indicates that the patient has ACTH-Independent Cushing's syndrome.

In embodiments, the methods disclosed herein typically include steps of measuring cortisol in a sample from the patient before administering the GRA, and of measuring the level or activity of cortisol in a sample from the patient after administering the GRA to determine whether or not there has been an increase in the level of cortisol. A determination that the level of cortisol has risen following GRA administration, whether or not accompanied by a rise in ACTH following GRA administration, indicates that the patient has ACTH dependent Cushing's syndrome. A determination that the level of cortisol has not risen following GRA administration, whether or not accompanied by a failure of ACTH to rise following GRA administration, indicates that the patient has ACTH-Independent Cushing's syndrome.

In embodiments, the methods disclosed herein may include steps of measuring adrenal hormones or adrenal pre-hormones in a sample from the patient before administering the GRA, and of measuring the level or activity of adrenal hormones or adrenal pre-hormones in a sample from the patient after administering the GRA to determine whether or not there has been an increase in the level of adrenal hormones or adrenal pre-hormones. A determination that the level of adrenal hormones or adrenal pre-hormones has risen following GRA administration, whether or not accompanied by a rise in ACTH following GRA administration, indicates that the patient has ACTH dependent Cushing's syndrome. A determination that the level of adrenal hormones or adrenal pre-hormones has not risen following GRA administration, whether or not accompanied by a failure of ACTH to rise following GRA administration, indicates that the patient has ACTH-Independent Cushing's syndrome.

The methods disclosed herein provide advantages of treating Cushing's syndrome in a patient suffering from Cushing's syndrome, while at the same time providing further diagnostic information useful for determining whether or not the patient has ACTH-Dependent Cushing's syndrome, and at the same time providing further diagnostic information useful for determining whether or not the patient has ACTH-Independent Cushing's syndrome. Such differential diagnosis, provided while the patient is already receiving appropriate treatment, avoids unnecessary delay in treating a serious medical condition, while aiding in specifying whether or not further treatment is needed, and aiding in identifying what type of further treatment may be needed (e.g., typically transsphenoidal surgery for patients identified as having ACTH-Dependent Cushing's syndrome; surgery for removal or resection of an ectopic tumor for patients identified as having ectopic ACTH-Dependent Cushing's syndrome; adrenal surgery for ACTH-Independent Cushing's patients identified as having an adrenal tumor causing adrenal Cushing's syndrome).

Other objects, features, and advantages of the methods disclosed herein will be apparent to one of skill in the art from the following detailed description.

DETAILED DESCRIPTION

I. Introduction

Novel methods are disclosed for treating and diagnosing forms of Cushing's syndrome and other disorders affecting adrenocorticotropic hormone (ACTH, also known as corticotropin) levels, cortisol levels, or both. Novel methods for Cushing's syndrome treatment and differential diagnosis between ACTH-Dependent Cushing's syndrome and ACTH-Independent Cushing's syndrome include methods in which a glucocorticoid receptor antagonist (GRA) is administered to a Cushing's syndrome patient with a basal ACTH level less than about 25 picograms per milliliter (pg/mL); a) if i) the patient's plasma or serum ACTH and ii) the patient's cortisol, or adrenal hormone, or adrenal pre-hormone levels rise, ACTH-Dependent Cushing's syndrome is diagnosed; b) if those levels do not rise, ACTH-Independent Cushing's syndrome is diagnosed. In some instances, the patient is recovering from surgery to remove an ACTH secreting tumor, and the method described herein is used to determine if the tumor resection was successful or complete. The GRA may be mifepristone, or a non-steroidal GRA having a heteroaryl-ketone fused azadecalin backbone (e.g., relacorilant), or an octahydro fused azadecalin backbone (e.g., exicorilant), or a cyclohexyl pyrimidine backbone (e.g., miricorilant), or a fused azadecalin backbone.

The novel methods include methods for treating and diagnosing forms of Cushing's syndrome and other disorders affecting ACTH levels, adrenal hormone or adrenal pre-hormone levels, or both ACTH and adrenal pre-hormone/hormone levels. In embodiments, a subject has a pituitary disorder, such as a pituitary tumor, which may secrete corticotropic releasing hormone (CRH), or ACTH, or cortisol, or all three. A pituitary tumor which secretes ACTH may cause ACTH-Dependent Cushing's syndrome. In embodiments, a subject has a non-pituitary tumor which may secrete ACTH and cause ectopic Cushing's syndrome, a form of ACTH-Dependent Cushing's syndrome. In embodiments, a subject has an adrenal disorder, such as an adrenal tumor, which may secrete cortisol and cause ACTH-Independent Cushing's syndrome. The methods include selecting a Cushing's syndrome patient having a basal plasma or serum cortisol level, and having a basal plasma or serum ACTH level that is less than about 25 pg/mL, e.g., between about 5 to 25 pg/mL; administering a glucocorticoid receptor antagonist (GRA) to said patient; and, as compared to their respective basal levels, a) if one or both of the patient's ACTH and cortisol levels rise after GRA administration, determining that the patient has ACTH-Dependent Cushing's syndrome; orb) if neither the patient's ACTH nor cortisol levels rise after GRA administration, determining that: the patient has ACTH-Independent Cushing's syndrome. In embodiments of the methods for treating and diagnosing forms of Cushing's syndrome disclosed herein, the basal plasma or serum ACTH level for selecting a patient with Cushing's syndrome that is less than about 25 pg/mL is less than about 20 pg/mL; or is less than about 15 pg/mL; or is less than about 10 pg/mL; or is less than about 5 pg/mL; or is detectable and is less than about 5 pg/mL. In further embodiments of the methods disclosed herein, the basal plasma or serum ACTH level for selecting a patient with Cushing's syndrome that is less than about 25 pg/mL is below the detectable level. In embodiments of the methods disclosed herein, the basal plasma or serum ACTH level for selecting a patient with Cushing's syndrome that is less than about 25 pg/mL is between about 5 to about 25 pg/mL. In embodiments of the methods disclosed herein, the basal plasma or serum ACTH level for selecting a patient with Cushing's syndrome that is less than about 25 pg/mL is between about 5 to about 20 pg/mL. In embodiments of the methods disclosed herein, the basal plasma or serum ACTH level for selecting a patient with Cushing's syndrome that is less than about 25 pg/mL is between about 5 to about 15 pg/mL.

In embodiments, Applicant further provides novel methods for treating and diagnosing forms of Cushing's syndrome, wherein the methods include selecting a Cushing's syndrome patient having a basal plasma or serum adrenal hormone or adrenal pre-hormone level, and having a basal plasma or serum ACTH level that is less than about 25 pg/mL, e.g., between about 5 to 25 pg/mL; administering a glucocorticoid receptor antagonist (GRA) to said patient; and, as compared to their respective basal levels, a) if one or both of the patient's ACTH and adrenal hormone or adrenal pre-hormone levels rise after GRA administration, determining that the patient has ACTH-Dependent Cushing's syndrome; or b) if neither the patient's ACTH nor adrenal hormone or adrenal pre-hormone levels rise after GRA administration, determining that the patient has ACTH-Independent Cushing's syndrome. Adrenal hormones and adrenal pre-hormones include, without limitation, 17α-hydroxy pregnenolone, 17α-hydroxy progesterone, 11-deoxycortisol, pregnenolone, progesterone, 11-deoxycorticosterone, corticosterone, 18-hydroxycorticosterone, aldosterone, dehydroepiandrosterone (androstenolone, DHEA), dehydroepiandrosterone sulfate (DHEA-S), and androstenedione. In embodiments of the methods for treating and diagnosing forms of Cushing's syndrome disclosed herein, the basal plasma or serum ACTH level for selecting a patient with Cushing's syndrome that is less than about 25 pg/mL is less than about 20 pg/mL; or is less than about 15 pg/mL; or is less than about 10 pg/mL; or is less than about 5 pg/mL. In further embodiments of the methods disclosed herein, the basal plasma or serum ACTH level for selecting a patient with Cushing's syndrome that is less than about 25 pg/mL is below the detectable level. In embodiments of the methods disclosed herein, the basal plasma or serum ACTH level for selecting a patient with Cushing's syndrome that is less than about 25 pg/mL is between about 5 to about 25 pg/mL. In embodiments of the methods disclosed herein, the basal plasma or serum ACTH level for selecting a patient with Cushing's syndrome that is less than about 25 pg/mL is between about 5 to about 20 pg/mL. In embodiments of the methods disclosed herein, the basal plasma or serum ACTH level for selecting a patient with Cushing's syndrome that is less than about 25 pg/mL is between about 5 to about 15 pg/mL.

In embodiments, the novel methods for treating and diagnosing forms of Cushing's syndrome include selecting a Cushing's syndrome patient having a basal plasma or serum adrenal hormone or adrenal pre-hormone level, and having a basal plasma or serum ACTH level that is less than about 25 pg/mL, e.g., between about 5 to 25 pg/mL; determining a ratio between the ACTH level and the cortisol level (the basal ACTH:cortisol ratio); administering a glucocorticoid receptor antagonist (GRA) to said patient; determining a ratio between the ACTH level and the cortisol level (the after-GRA ACTH:cortisol ratio); comparing the basal ACTH:cortisol ratio to the after-GRA ACTH:cortisol ratio; and differentially diagnosing between adrenocorticotropin hormone (ACTH)-Dependent Cushing's syndrome and ACTH-Independent Cushing's syndrome based on said comparison between the basal ACTH:cortisol ratio and the after-GRA ACTH:cortisol ratio, wherein:

if the basal ACTH:cortisol ratio is greater than the after-GRA ACTH:cortisol ratio, then the patient is diagnosed with ACTH-independent Cushing's syndrome; and if the basal ACTH:cortisol ratio is smaller than the after-GRA ACTH:cortisol ratio, then the patient is diagnosed with ACTH-dependent Cushing's syndrome, Whereby Cushing's syndrome is treated and differential diagnosis between a) ACTH-Dependent Cushing's syndrome and between b) ACTH-Independent Cushing's syndrome is obtained. Thus, if the ACTH:cortisol ratio decreases after GRA administration, then the patient is diagnosed with ACTH-independent Cushing's syndrome. If the ACTH:cortisol ratio increases after GRA administration, then the patient is diagnosed with ACTH-dependent Cushing's syndrome. An ACTH:cortisol ratio is calculated by dividing the numerical value of the ACTH level (e.g., the plasma or serum ACTH level) by the numerical value of the cortisol level (e.g., the plasma or serum cortisol level). In embodiments, the change in ACTH:cortisol ratio from before GRA treatment to after GRA treatment is at least about 5%, or at least about 10%, or at least about 15%, or at least about 20%, or is greater than about 25% of the value of the basal ACTH:cortisol ratio.

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

As used herein, the term "resection," in the context of a tumor, refers to surgical ablation or removal of a tumor, effective to reduce the size of the tumor by removal of tumor tissue from the patient, and, in the best case, to remove all of the tumor tissue from the patient. The term "complete resection," in the context of a tumor, refers to surgical removal of a tumor such that the tumor no longer affects ACTH levels in the subject. Complete resection can refer to eliminating all of the visible tumor, e.g., pituitary tumor. In some cases, complete resection includes surgical removal of a tumor to provide the subject with a considerable clinical benefit or a curative benefit.

The term "Cushing's syndrome" refers to a disease caused by prolonged exposure to excess glucocorticoids. Cushing's syndrome patients often suffer hyperglycemia secondary to hypercortisolism. Symptoms of Cushing's syndrome include, but are not limited to one or more of the following: weight gain, high blood pressure, poor short term memory, poor concentration, irritability, excess hair growth, impaired immunological function, ruddy complexion, extra fat in the neck region, moon face, fatigue, red stretch marks, irregular menstruation, or a combination thereof. Symptoms of Cushing's syndrome can additionally or alternatively include without limitation one or more of the following: insomnia, recurrent infection, thin skin, easy bruising, weak bones, acne, balding, depression, hip or shoulder weakness, swelling of the extremities, diabetes mellitus, elevated white blood cell count, hypokalemic metabolic alkalosis, or a combination thereof.

Normally, cortisol is secreted by the adrenal glands in response to ACTH secretion from the pituitary (which ACTH secretion is in response to secretion of corticotropin releasing hormone (CRH) from the hypothalamus). Cushing's syndrome may be caused, for example, by overproduction of cortisol caused by a pituitary ACTH-secreting tumor (Cushing's disease), a non-pituitary ACTH-secreting tumor, or a cortisol-secreting tumor (e.g., an adrenal tumor). ACTH-secreting tumors can be, e.g., pituitary adenomas, pituitary adenocarcinomas, carincinoid tumors and neuroendocrine tumors. Cortisol-secreting tumors include, and are not limited to, cortisol producing adrenal adenomas, adrenocortical carcinomas, primary pigmented micronodular adrenal disease (PPNAD), ACTH independent macronodular adrenal hyperplasia (AIMAH), and extra-adrenal cortisol secreting tumors, e.g., ovarian carcinomas.

The term "ACTH-Dependent Cushing's syndrome" refers to Cushing's syndrome caused by excess ACTH secretion, by a pituitary or a non-pituitary tumor. ACTH-Dependent Cushing's syndrome" caused by excess ACTH secretion from a pituitary tumor is called Cushing's Disease. ACTH-Dependent Cushing's syndrome may also be caused by excess ACTH secretion from a non-pituitary tumor, which is called an "ectopic" tumor.

The term "ACTH-Independent Cushing's syndrome" refers to a disease of excess cortisol that may be caused by, e.g., an adrenal tumor that secretes cortisol. The excess cortisol levels experienced by the patient are not dependent on ACTH levels.

The term "pituitary tumor" refers to a tumor located in, or near to, the pituitary gland or its stalk. As used herein the term "pituitary tumor" includes, but is not limited to, lactotrophic adenoma or prolactinoma, ACTH-secreting adenoma, somatotrophic adenomas, corticotrophic adenoma, gonadotrophic adenoma, thyrotrophic adenomas, and null cell adenoma. An ACTH-secreting pituitary tumor may be found in the anterior lobe of the pituitary, usually measuring less than about 5 millimeters (mm) in diameter. Most pituitary ACTH-secreting adenomas are small in size (i.e., microadenomas), although many such tumors are macroadenomas (i.e., sized greater than 10 mm in at least one dimension).

"Patient," "individual" or "subject" is used interchangeably to refer to a human subject, and typically to a human subject suffering from a disease or condition to be diagnosed and/or treated. A patient is a human subject who may be in need of, or is suspected of having a need for, treatment.

The term "selecting a patient having a basal level of plasma or serum cortisol, and having a detectable basal level of plasma or serum ACTH" refers to identifying a human subject with a detectable level of cortisol in a plasma or serum sample, and having a detectable level of ACTH in a plasma or serum sample, where the sample was obtained prior to GRA treatment ("basal" referring to a baseline, or initial, measurement taken before GRA treatment). The ACTH level may be, for example, less than 25 pg/mL. The cortisol level and the ACTH level can be determined according to methods known to those in the art including those described below.

The term "morning plasma level of cortisol" refers to the level, amount or concentration of cortisol in plasma in the morning, e.g., between about 7 a.m. to about 9 a.m. To measure a patient's morning plasma level of cortisol, samples are drawn from the patient with normal circadian rhythms (e.g., a nighttime sleep cycle) between 7 a.m. and 9 a.m. The normal range of serum cortisol in the morning is about 4 micrograms per deciliter (μg/dL) to about 28 μg/dL. To convert from μg/dL cortisol to nanomoles per liter (nmol/L) cortisol, multiply by the cortisol conversion factor (27.59).

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, transdermal patches, etc.

The term "sample" refers to a biological sample obtained from a human subject. Such samples are typically removed from the subject, and, when obtained, become entirely separate from the subject (i.e., are in vitro samples). The sample can be any cell, tissue or fluid sample obtained from a human subject. The sample may be, e.g., a blood sample, a saliva sample, a urine sample, or other sample obtained from the patient. Samples can be subject to various treatment, storage or processing procedures before being analyzed according to the methods described herein. Generally, the terms "sample" or "samples" are not intended to be limited by their source, origin, manner of procurement, treatment, processing, storage or analysis, or any modification. Thus, in embodiments, samples are in vitro samples and may be analyzed using in vitro methods. The methods disclosed herein are in vitro methods when used with samples obtained from, and removed from, the human subject.

The term "cortisol" refers to the naturally occurring glucocorticoid hormone (also known as hydrocortisone) that is produced by the zona fasciculata of the adrenal gland. Cortisol has the structure:

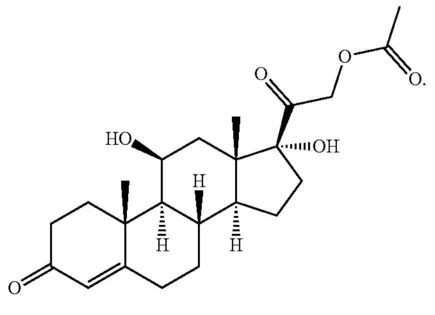

The term "total cortisol" refers to cortisol that is bound to cortisol-binding globulin (CBG or transcortin) and free cortisol (cortisol that is not bound to CBG). The term "free cortisol" refers to cortisol that is not bound to cortisol-binding globulin (CBG or transcortin). As used herein, the term "cortisol" refers to total cortisol, free cortisol, and/or cortisol bound of CBG.

The term "adrenocorticotropic hormone" or "ACTH" refers to a polypeptide-based hormone that is normally produced and secreted by the anterior pituitary gland. ACTH stimulates secretion of cortisol and other glucocorticoids (GCs) by specialized cells of the adrenal cortex. In healthy mammals, ACTH secretion is tightly regulated. ACTH secretion is positively regulated by corticotropin releasing hormone (CRH), which is released by the hypothalamus. ACTH secretion is negatively regulated by cortisol and other glucocorticoids.

The terms "adrenal hormone", "adrenal pre-hormone", and "adrenal hormone or adrenal pre-hormone" refer to steroid molecules that are, or are precursors of, hormones produced by the adrenal gland. As used herein, without limitation, an "adrenal hormone or adrenal pre-hormone" may be one or more of 17α-hydroxy pregnenolone, 17α-hydroxy progesterone, 11-deoxycortisol, pregnenolone, progesterone, 11-deoxycorticosterone, corticosterone, 18-hydroxycorticosterone, aldosterone, dehydroepiandrosterone (androstenolone, DHEA), dehydroepiandrosterone sulfate (DHEA-S), and androstenedione. As used herein, the terms "adrenal hormone", "adrenal pre-hormone", and "adrenal hormone or adrenal pre-hormone" refer to hormones and pre-hormones other than cortisol unless it is explicitly stated that cortisol in intended to be included as well.

The term "detectable," in the context of a level of ACTH, cortisol, adrenal hormone, adrenal pre-hormone, or other analyte, refers to a level of that analyte in a sample that can be differentiated from (determined to be different from) the zero or "blank" level of the particular measuring device or measurement technique used to determine the analyte level. Such measurements may be performed by any suitable assay method, including, without limitation, e.g., radioimmunoassays, immunofluorometric enzyme assays, enzyme-linked immunosorbent assays, a competitive protein-binding assay, liquid chromatography (including HPLC), mass spectroscopy, light intensity in a dye-based measurement, binding assays, and other assays using other devices and techniques.

The term "measuring the level," in the context of ACTH, cortisol, adrenal hormone, adrenal pre-hormone, or other hormone or other steroid, refers to determining, detecting, or quantitating the amount, level, or concentration of, for example, cortisol, ACTH or other steroid in a sample obtained from a subject. The sample may be, e.g., a blood sample, a saliva sample, a urine sample, or other sample obtained from the patient. A level may be measured from a fraction of a sample. For example, a level (e.g., ACTH or cortisol) may be measured in the plasma fraction of a blood sample; may be measured in a serum fraction of a blood sample; or, in embodiments, may be measured in whole blood.

The term "low level," in the context of cortisol, ACTH or other steroid, refers an amount, level, or concentration of, for example, cortisol, ACTH or other steroid in a sample obtained from a subject that is below (less than) a standard control level or a control level in a sample obtained from a normal, healthy subject, such as a subject with a normally functioning HPA axis.

An "increase" or "rise" refers to a detectable positive change in quantity from an initial level, or baseline, and may be made in comparison to a control, e.g., an established standard control (such as an average level of cortisol in a normal, healthy subject who does not have Cushing's syndrome). An increase or rise is a positive change that is typically at least 5%, at least 10%, or at least 20%, or 50%, or 100%, and can be as high as at least 1.5-fold, at least 2-fold, at least 5-fold or even 10-fold of the control value. Other terms indicating quantitative changes or differences from a comparative basis, such as "more" and "higher" are used in this application in the same fashion as described above.

A "decrease" refers to a detectable negative change in quantity from an initial level, or baseline, and may be made in comparison to a control, e.g., an established standard control (such as an average level of cortisol in a normal, healthy subject who does not have Cushing's syndrome). A decrease is a negative change that is typically at least 5%, at least 10%, or at least 20%, 30%, or 50%, or even as high as at least 80% or 90% of the control value. Other terms indicating quantitative changes or differences from a comparative basis, such as e.g.," "less" and "lower" are used in this application in the same fashion as described above.

The term "standard control level" as used herein refers to a predetermined amount, level or concentration of cortisol in an established biological sample, e.g., a serum sample from a normal, healthy subject. The standard control value is suitable for the use of a method of the present invention, to serve as a basis for comparing the level of total and/or free cortisol that is present in a test sample after administering a GRA to the test subject. An established sample serving as a standard control provides an average level of cortisol in normal, healthy subjects after administration of a GRA. A standard control value may vary depending on the nature of the sample, the manner of sample collection, as well as other factors such as the sex, age, ethnicity of the subjects based on whom such a control value is established.

The term "chromatography" refers to a process in which a chemical mixture carried by a liquid or gas is separated into components as a result of differential distribution of the chemical entities as they flow around or over a stationary liquid or solid phase.

The term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

The term "high performance liquid chromatography" or "HPLC" (also sometimes known as "high pressure liquid chromatography") refers to liquid chromatography in which the degree of separation is increased by forcing the mobile phase under pressure through a stationary phase, typically a densely packed column. As used herein, the term "ultra high performance liquid chromatography" or "HPLC" or "UHPLC" (sometimes known as "ultra high pressure liquid chromatography") refers to HPLC which occurs at much higher pressures than traditional HPLC techniques.

The term "glucocorticoid" ("GC") includes any compound known in the art that is referred to as a glucocorticoid receptor agonist, glucocorticoid, glucocorticosteroid, corticoid, corticosteroid, or steroid that binds to and activates a glucocorticoid receptor. "Glucocorticosteroid" refers to a steroid hormone or steroidal molecule that binds to the glucocorticoid receptor. Glucocorticosteroids are GCs. Glucocorticosteroids are typically characterized by having 21 carbon atoms, an α,β-unsaturated ketone in ring A, and an α-ketol group attached to ring D. They differ in the extent of oxygenation or hydroxylation at C-11, C-17 and C-19 (Rawn, "Biosynthesis and Transport of Membrane Lipids and Formation of Cholesterol Derivatives," in Biochemistry, Daisy et al. (eds.), 1989, pg. 567).

"Glucocorticoid receptor" ("GR") refers to the type II GR which specifically binds to cortisol and/or cortisol analogs such as dexamethasone (See, e.g., Turner & Muller, *J Mol Endocrinol,* 2005 35 283-292). The GR is also referred to as the cortisol receptor. The term includes isoforms of GR, recombinant GR and mutated GR. Inhibition constants (Ki) against the human GR receptor type II (Genbank: P04150) are between 0.0001 nM to 1,000 nM; preferably between 0.0005 nM to 10 nM, and most preferably between 0.001 nM to 1 nM.

The term "glucocorticoid receptor antagonist" or "GRA" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," the drug preferentially binds to the GR rather than other nuclear receptors, such as mineralocorticoid receptor (MR), androgen receptor (AR), or progesterone receptor (PR). It is preferred that the specific glucocorticoid receptor antagonist bind GR with an affinity that is 10× greater (1/10th the Kd value) than its affinity to the MR, AR, or PR, both the MR and PR, both the MR and AR, both the AR and PR, or to the MR, AR, and PR. In a more preferred embodiment, the specific glucocorticoid receptor antagonist binds GR with an affinity that is 100× greater (1/100th the Kd value) than its affinity to the MR, AR, or PR, both the MR and PR, both the MR and AR, both the AR and PR, or to the MR, AR, and PR.

The term "selective inhibitor" in the context of glucocorticoid receptor, refers to a chemical compound that selectively interferes with the binding of a specific glucocorticoid receptor agonist and the glucocorticoid receptor.

The term "steroidal backbone" in the context of steroid molecules and glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

Formula I

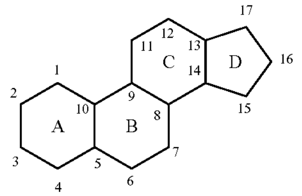

Steroidal Backbone

The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33: 557-563).

As used herein, the term "mifepristone" refers to 11β-(4-dimethylaminophenyl)-17β-hydroxy-17α-(1-propynyl)-estra-4,9-dien-3-one), also referred to as RU486, or as RU38.486, or as 17-beta-hydroxy-11-beta-(4-dimethyl-aminophenyl)-17-alpha-(1-propynyl)-estra-4,9-dien-3-one). Mifepristone binds to the glucocorticoid receptor (GR), typically with high affinity, and inhibits the biological effects initiated/mediated by the binding of any cortisol or cortisol analogue to a GR receptor. Salts, hydrates and prodrugs of mifepristone are all included in the term "mifepristone" as used herein. Thus, used herein, "mifepristone" refers to the molecule that has the following structure:

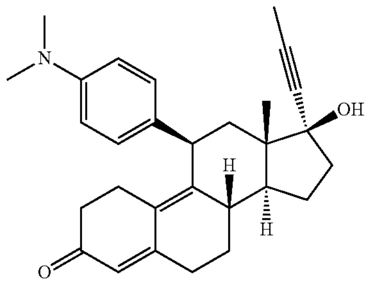

and to salts, hydrates and prodrugs thereof, and pharmaceutical compositions thereof.

As used herein, the phrase "non-steroidal backbone" in the context of glucocorticoid receptor antagonists containing such refers to glucocorticoid receptor antagonists that do not share structural homology to, or are not modifications of, cortisol. Such compounds include synthetic mimetics and analogs of proteins, including partially peptidic, pseudopeptidic and non-peptidic molecular entities.

Non-steroidal GRA compounds also include glucocorticoid receptor antagonists having a cyclohexyl-pyrimidine backbone, a fused azadecalin backbone, a heteroaryl ketone fused azadecalin backbone, or an octahydro fused azadecalin backbone. Exemplary glucocorticoid receptor antagonists having a cyclohexyl-pyrimidine backbone include those described in U.S. Pat. Nos. 8,685,973; 8,906,917; and 9,321,736. Exemplary glucocorticoid receptor antagonists having a fused azadecalin backbone include those described in U.S. Pat. Nos. 7,928,237; and 8,461,172. Exemplary heteroaryl-ketone fused azadecalin compounds are described in U.S. Pat. Nos. 8,859,774; 9,273,047; 9,707,223; and 9,956,216. Exemplary glucocorticoid receptor antagonists having an octohydro fused azadecalin backbone include those described in U.S. Pat. No. 10,047,082. All patents, patent applications, and patent publications are hereby incorporated by reference herein in their entireties.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

All patents, patent applications, patent publications, and international patents, and references cited herein are hereby incorporated by reference in their entireties.

III. Methods of Treatment and Differential Diagnosis

Cushing's syndrome is typically associated with hypercortisolemia (excess cortisol). Other symptoms and disorders associated with Cushing's syndrome include hypertension, hyperglycemia, diabetes, hypercoagulopathy (proneness to blood clotting), hypokalemia (low potassium levels), upper-body obesity, rounded face, increased fat around the neck, thinning arms and legs, easy bruising, facial plethora, acne, red purple stripes across the body, severe fatigue, weak muscles, irritability, anxiety, cognitive disturbances and depression. Treatment of such hypercortisolemia typically treats, or ameliorates, other symptoms and disorders associated with hypercortisolemia. Cushing's syndrome patients often suffer hyperglycemia secondary to hypercortisolism.

Cushing's syndrome may be diagnosed without knowledge of the source of the excess cortisol or GC action which characterizes the syndrome. Thus, while treatment (e.g., administration of a GRA such as mifepristone) may begin, further diagnostic information may need to be acquired in order to provide the patient with the best treatment for their condition. The present methods provide GRA treatment, and at the same time utilize that treatment to acquire further information effective to determine whether the patient suffers from ACTH-Dependent Cushing's syndrome, or whether the patient suffers from ACTH-Independent Cushing's syndrome. Thus, the present methods provide advantages including treatment administered concurrent with diagnostic steps related to (further) treatment of Cushing's syndrome and related disorders.

In some cases, pituitary tumors are not visible on MM, posing significant challenges for surgical resection. In other cases, the tumors are large and may impinge upon surrounding critical structures, thus hampering complete tumor resection. Extensive surgical resection may cause significant damage to normal pituitary tissue leading to hypopituitarism, and in some cases adrenal insufficiency. The methods provided herein can be used to determine whether a patient suffers from ACTH-Dependent Cushing's syndrome (and has, e.g., a pituitary tumor, or an ectopic tumor), or suffers from ACTH-Independent Cushing's syndrome (and has, e.g., an adrenal tumor). The methods are also useful for postoperative determination of whether a subject has had complete or successful resection of an ACTH-secreting tumor.

The methods include obtaining biological samples from a patient suffering from Cushing's syndrome. The biological sample can be saliva, urine, whole blood, plasma, serum, or another biological sample from the patient. In some embodiments, the biological sample is a blood sample. In embodiments, one or both of ACTH and cortisol are measured in plasma from a blood sample obtained from a Cushing's syndrome patient. In embodiments, one or both of ACTH and cortisol are measured in serum from a blood sample obtained from a Cushing's syndrome patient. In embodiments, adrenal hormones or adrenal pre-hormones are measured in plasma from a blood sample obtained from a Cushing's syndrome patient. In embodiments, adrenal hormones or adrenal pre-hormones are measured in serum from a blood sample obtained from a Cushing's syndrome patient. In some embodiments, the biological sample is saliva. In other embodiments, the biological sample is urine. In embodiments, the sample may be any biological fluid that is not whole blood, plasma or serum.

ACTH Assay

The method described herein includes measuring the level of adrenocorticotropic hormone (ACTH) in a biological sample from a patient suffering from Cushing's syndrome. Similar to cortisol levels, adrenocorticotropic hormone (ACTH) levels are highest in the morning from about 6-8 a.m. (i.e., about 0600 h-about 0800 h) and lowest at about 11 p.m (i.e., about 2300 h). Generally, normal ACTH levels in the morning are about 10-60 pg/ml, varying depending on assay method. In some embodiments of the present method, the level of ACTH is measured in a biological sample from the subject to determine whether the subject has ACTH-Dependent Cushing's syndrome, or ACTH-Independent Cushing's syndrome. The biological sample may be serum, plasma, saliva, urine, or any other biological fluid taken from a subject. In some cases, the same sample is used to measure cortisol level and ACTH level. In other cases, different samples are used to measure cortisol and ACTH levels. For example, cortisol levels can be measured in saliva or urine, and ACTH levels can be measured in plasma. In yet other cases, different samples of the same type are used to measure the levels.

The level of ACTH can be measured using various methods such as, but not limited to, immunoassays, e.g., competitive immunoassay, radioimmunoassay, immunofluorometric enzyme assay, and ELISA, competitive protein-binding assays, liquid chromatography (e.g., HPLC), and mass spectrometry, e.g., high-performance liquid chromatography/triple quadrupole-mass spectrometry (LC-MS/MS).

Cortisol Assay

Cortisol levels can be measured in a biological sample, such as saliva, urine, whole blood, serum, plasma, or any other biological fluid taken from a patient suffering from Cushing's syndrome. In blood (e.g., plasma or serum), normal cortisol levels in the morning typically range from about 5 to 20 micrograms per deciliter (μg/dL) (corresponding to about 140 to about 690 nanomoles per liter (nmol/L)); later in the day, such cortisol levels may range from about 3 to about 10 (μg/dL) (corresponding to about 80 to about 275 nmol/L) Cortisol levels in Cushing's syndrome patients may be much greater (e.g., may range from about 10 μg/dL to about 36 μg/dL or more (corresponding to 250 to about 1000 or more nmol/L). In some cases, the same sample is used to measure cortisol level and ACTH level. In other cases, different samples are used to measure cortisol and ACTH levels. For example, cortisol levels can be measured in saliva or urine, and ACTH levels can be measured in plasma. In yet other cases, different samples of the same type are used to measure the levels. Methods for measuring cortisol levels are known to those in the art. Useful assays include immunoassays, e.g., competitive immunoassay, radioimmunoassay, immunofluorometric enzyme assay, and ELISA, competitive protein-binding assay and mass spectrometry, e.g., high-performance liquid chromatography/triple quadrupole-mass spectrometry (LC-MS/MS). Commercial kits for measuring cortisol in sample are available from, e.g., Beckman-Coulter, Seimens, Roche Diagnostics, and the like. Non-limiting examples of an immunoassay include an ADVIA Centaur® Cortisol assay (Siemens Healthcare Global), ARCHITECT i2000SR cortisol (Abbott), Immulite® 2000 Cortisol assay (Siemans Healthcare Global; #L2KCO2), Vitros® ECi Cortisol assay (Ortho Clinical Diagnostics; #107 4053), and Elecsys® Cortisol Immunoassay (Roche Molecular Diagnostics; #11875116160).

Assays for Adrenal Hormones and Pre-Hormones

Levels of adrenal hormones and pre-hormones can be measured in a biological sample, such as saliva, urine, whole blood, serum, plasma, or any other biological fluid taken from a patient suffering from Cushing's syndrome. In some cases, the same sample is used to measure ACTH level and to measure levels of adrenal hormones or pre-hormones. In other cases, different samples are used to measure ACTH levels and levels of adrenal hormones and pre-hormones. For example, adrenal hormone and pre-hormone levels can be measured in saliva or urine, and ACTH levels can be measured in plasma. In yet other cases, different samples of the same type are used to measure the levels. Methods for measuring adrenal hormone and pre-hormone levels are known to those in the art. Useful assays include immunoassays, e.g., competitive immunoassay, radioimmunoassay, immunofluorometric enzyme assay, and ELISA, competitive protein-binding assay and mass spectrometry, e.g., high-performance liquid chromatography/triple quadrupole-mass spectrometry (LC-MS/MS).

Administration of a Glucocorticoid Receptor Antagonist

Any suitable GRA dose may be used in the methods disclosed herein. In embodiments, the GRA is administered orally. The dose of GRA that is administered can be at least about 50 milligrams (mg) per day, or about 100 mg/day, or about 200 mg/day, or about 300 mg/day, or about 400 mg/day, or about 500 mg/day, or about 600 mg/day, e.g., about 600 mg/day, about 700 mg/day, about 800 mg/day, about 900 mg/day, about 1000 mg/day, about 1100 mg/day, about 1200 mg/day, or more. For example, where the GRA is mifepristone, the GRA dose may be, e.g., 300 mg/day, or 600 mg/day, or 900 mg/day, or 1200 mg/day of mifepristone. For example, where the GRA is relacorilant, the GRA dose may be, e.g., 25 mg/day, or 50 mg/day, or 100 mg/day, or 150 mg/day, or 200 mg/day, or 250 mg/day, or 300 mg/day, or 350 mg/day, or 400 mg/day, or 450 mg/day, or 500 mg/day, or 550 mg/day of relacorilant. In some embodiments, the GRA is administered in at least one dose. In other words, the GRA can be administered in 1, 2, 3, 4, 5, 6, 7, 8, 9, 10 or more doses. In embodiments, the GRA is administered orally in 1, 2, 3, 4, 5, 6, 7, 8, 9, 10 or more doses.

After it has been determined that the subject has a) a basal cortisol level, e.g., a basal plasma or serum cortisol level (and optionally a basal level of an adrenal hormone or pre-hormone as well, or in place of cortisol), and b) a basal level of plasma or serum ACTH that is less than about 25 pg/mL (e.g., between about 5 to 25 pg/mL), the subject is administered at least one dose of glucocorticoid receptor antagonist (GRA) in one or more doses over, for example, a 2-48 hour period. In some embodiments, the GRA is administered as a single dose. In other embodiments, the GRA is administered in more than one dose, e.g. 2 doses, 3 doses, 4 doses, 5 doses, or more doses over a 2-48 hour period, e.g., a 2 hour period, a 3 hour period, a 4 hour period, a 5 hour period, a 6 hour period, a 7 hour period, a 8 hour period, a 9 hour period, a 10 hour period, a 11 hour period, a 12 hour period, a 14 hour period, a 16 hour period, a 18 hour period, a 20 hour period, a 22 hour period, a 24 hour period, a 26 hour period, a 28 hour period, a 30 hour period, a 32 hour period, a 34 hour periods a 36 hour periods a 38 hour period, a 40 hour period, a 42 hour period, a 44 hour period, a 46 hour period or a 48 hour period. In some embodiments, the GRA is administered over 2-48 hours, 2-36 hours, 2-24 hours, 2-12 hours, 2-8 hours, 8-12 hours, 8-24 hours, 8-36 hours, 8-48 hours, 9-36 hours, 9-24 hours, 9-20 hours, 9-12 hours, 12-48 hours, 12-36 hours, 12-24 hours, 18-48 hours, 18-36 hours, 18-24 hours, 24-36 hours, 24-48 hours, 36-48 hours, or 42-48 hours.

In embodiments, a basal level of an adrenal hormone or pre-hormone may be measured in addition to measuring a basal cortisol level, or, in embodiments, may be measured in place of cortisol. Thus, in embodiments, after it has been determined that the subject has a) a basal cortisol level, e.g., a basal plasma or serum cortisol level (and optionally a basal level of an adrenal hormone or pre-hormone as well, or in place of cortisol), and b) a basal level of plasma or serum ACTH that is less than about 25 pg/mL (e.g., between about 5 to 25 pg/mL), the subject is administered at least one dose of glucocorticoid receptor antagonist (GRA) in one or more doses over, for example, a 2-48 hour period. In some embodiments, the GRA is administered as a single dose. In other embodiments, the GRA is administered in more than one dose, e.g. 2 doses, 3 doses, 4 doses, 5 doses, or more doses over a 2-48 hour period, e.g., a 2 hour period, a 3 hour period, a 4 hour period, a 5 hour period, a 6 hour period, a 7 hour period, a 8 hour period, a 9 hour period, a 10 hour period, a 11 hour period, a 12 hour period, a 14 hour period, a 16 hour period, a 18 hour period, a 20 hour period, a 22 hour period, a 24 hour period, a 26 hour period, a 28 hour period, a 30 hour period, a 32 hour period, a 34 hour periods a 36 hour periods a 38 hour period, a 40 hour period, a 42 hour period, a 44 hour period, a 46 hour period or a 48 hour period. In some embodiments, the GRA is administered over 2-48 hours, 2-36 hours, 2-24 hours, 2-12 hours, 2-8 hours, 8-12 hours, 8-24 hours, 8-36 hours, 8-48 hours, 9-36 hours, 9-24 hours, 9-20 hours, 9-12 hours, 12-48 hours, 12-36 hours, 12-24 hours, 18-48 hours, 18-36 hours, 18-24 hours, 24-36 hours, 24-48 hours, 36-48 hours, or 42-48 hours.

After administration of a GRA, the level of ACTH, or cortisol, or both, is (or both are) again measured in a further sample obtained from the patient. If the patient's plasma or serum ACTH level in the further sample obtained after GRA administration is determined to be greater than the basal ACTH level, then the patient is diagnosed as suffering from ACTH-Dependent Cushing's syndrome. If the patient's plasma or serum cortisol level in the further sample obtained after GRA administration is determined to be greater than the basal cortisol level, then the patient is diagnosed as suffering from ACTH-Dependent Cushing's syndrome. If the levels of both ACTH and cortisol are determined in the further sample obtained after GRA administration to be greater than the basal ACTH and cortisol levels, respectively, then the patient is diagnosed as suffering from ACTH-Dependent Cushing's syndrome.

If a) the patient's plasma or serum ACTH level in the further sample obtained after GRA administration is determined not to be greater than the basal ACTH level, and b) the patient's plasma or serum cortisol level in the further sample obtained after GRA administration is determined not to be greater than the basal cortisol level, then the patient is diagnosed as suffering from ACTH-Independent Cushing's syndrome.

In embodiments in which an adrenal hormone or pre-hormone level has been measured, after administration of a GRA, the level of ACTH, or cortisol, or both (and optionally levels of an adrenal hormone and/or pre-hormone along with, or in place of, cortisol), are again measured in a further sample obtained from the patient. If the patient's plasma or serum ACTH level in the further sample obtained after GRA administration is determined to be greater than the basal ACTH level, then the patient is diagnosed as suffering from ACTH-Dependent Cushing's syndrome. If the patient's plasma or serum cortisol level (and/or adrenal hormone or pre-hormone level) in the further sample obtained after GRA administration is determined to be greater than the basal cortisol level, then the patient is diagnosed as suffering from ACTH-Dependent Cushing's syndrome. If the levels of both ACTH and cortisol (and/or adrenal hormone or pre-hormone level) are determined in the further sample obtained after GRA administration to be greater than the basal ACTH and cortisol levels, respectively, then the patient is diagnosed as suffering from ACTH-Dependent Cushing's syndrome.

In embodiments in which an adrenal hormone or pre-hormone level has been measured, after administration of a GRA, the level of ACTH, or cortisol, or both (and optionally levels of an adrenal hormone and/or pre-hormone as well as, or in place of cortisol), are again measured in a further sample obtained from the patient. If a) the patient's plasma or serum ACTH level in the further sample obtained after GRA administration is determined not to be greater than the basal ACTH level, and b) the patient's plasma or serum cortisol level (and/or adrenal hormone or pre-hormone level) in the further sample obtained after GRA administration is determined not to be greater than the basal cortisol level, then the patient is diagnosed as suffering from ACTH-Independent Cushing's syndrome.

The GRA can be a selective inhibitor of the glucocorticoid receptor. Alternatively, the GRA has a non-steroidal backbone. In some cases, the backbone of the GRA is a cyclohexyl pyrimidine, a fused azadecalin, a heteroaryl-ketone fused azadecalin, or an octahydro fused -azadecalin. Additional details of GRAs that can be used in the method provided herein are described below. The GRA may be administered once, or twice, or more times during a day. The GRA may be administered for one day; for two days; for three days; or for more days prior to obtaining the further sample after GRA administration that is used to determine the level of ACTH, or cortisol, or both.

The biological sample, e.g., plasma, serum, whole blood, urine, or saliva sample can be taken 2 to 48 hours, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 32, 35, 36, 37, 38, 39, 40, 41, 42, 43, 44, 45, 46, 47 or 48 hours after GRA administration. In some embodiments, the sample is taken from the patient 2 to 24 hours, e.g., 2, 3, 4, 5, 6, 7, 8, 9, 10, 11, 12, 13, 14, 15, 16, 17, 18, 19, 20, 21, 22, 23, or 24 hours after GRA administration.

As described above, ACTH and cortisol levels can be detected in the biological sample using various methods known to those in the art, such as, but not limited to, immunoassays, e.g., competitive immunoassay, radioimmunoassay, immunofluorometric assay, and ELISA, competitive protein-binding assay, liquid chromatography (e.g., HPLC), and mass spectrometry, e.g., high-performance liquid chromatography/triple quadrupole-mass spectrometry (LC/MS/MS).

As described above, adrenal hormone and adrenal pre-hormone levels can be detected in the biological sample using various methods known to those in the art, such as, but not limited to, immunoassays, e.g., competitive immunoassay, radioimmunoassay, immunofluorometric assay, and ELISA, competitive protein-binding assay, liquid chromatography (e.g., HPLC), and mass spectrometry, e.g., high-performance liquid chromatography/triple quadrupole-mass spectrometry (LC/MS/MS).

Glucocorticoid Receptor Antagonists

The methods of the present invention generally provide administering a glucocorticoid receptor antagonist (GRA). In some cases, the glucocorticoid receptor antagonist is a specific glucocorticoid receptor antagonist. As used herein, a specific glucocorticoid receptor antagonist refers to a composition or compound which inhibits any biological response associated with the binding of a glucocorticoid receptor to an agonist by preferentially binding to the glucocorticoid receptor rather than another nuclear receptor (NR). In some embodiments, the specific glucocorticoid receptor antagonist binds preferentially to glucocorticoid receptor rather than the mineralocorticoid receptor (MR), androgen receptor (AR), or progesterone receptor (PR). In an exemplary embodiment, the specific glucocorticoid receptor antagonist binds preferentially to glucocorticoid receptor rather than the mineralocorticoid receptor (MR). In another exemplary embodiment, the specific glucocorticoid receptor antagonist binds preferentially to glucocorticoid receptor rather than the progesterone receptor (PR). In another exemplary embodiment, the specific glucocorticoid receptor antagonist binds preferentially to glucocorticoid receptor rather than the androgen receptor (AR). In yet another exemplary embodiment, the specific glucocorticoid receptor antagonist binds preferentially to glucocorticoid receptor in comparison to MR and PR, MR and AR, PR and AR, or MR, PR, and AR.

In a related embodiment, the specific glucocorticoid receptor antagonist binds to the glucocorticoid receptor with an association constant (Kd) that is at least 10-fold less than the Kd for other nuclear receptors. In another embodiment, the specific glucocorticoid receptor antagonist binds to the glucocorticoid receptor with an association constant (Kd) that is at least 100-fold less than the Kd for the other nuclear receptors. In another embodiment, the specific glucocorticoid receptor antagonist binds to the glucocorticoid receptor with an association constant (Kd) that is at least 1000-fold less than the Kd for the other nuclear receptors.

Generally, treatment can be provided by administering an effective amount of a glucocorticoid receptor antagonist (GRA) of any chemical structure or mechanism of action and a glucocorticoid (GC) of any chemical structure or mechanism of action. Provided herein, are classes of exemplary GRAs and specific members of such classes. However, one of skill in the art will readily recognize other related or unrelated GRAs that can be employed in the treatment methods described herein.

Glucocorticoid antagonists with modified steroidal backbones comprising removal or substitution of the 1143 hydroxy group are administered in one embodiment of the invention. This class includes natural GRAs, including cortexolone, progesterone and testosterone derivatives, and synthetic compositions, such as mifepristone (Lefebvre, et al. supra). Mifepristone (17-β-hydrox-11-β-(4-dimethyl-aminophenyl)17-α-(1-propynyl)estra-4,9-dien-3-one)), also known as RU486, has been shown to be a powerful antagonist of both the glucocorticoid receptor (GR) and the progesterone receptor. Thus, in some embodiments, the GRA is mifepristone, or a salt, tautomer, or derivative thereof.

In some embodiments, the non-steroidal GRA useful for the practice of the methods disclosed herein has a cyclohexyl-pyrimidine backbone, a fused azadecalin backbone, a heteroaryl ketone fused azadecalin backbone, or an octahydro fused azadecalin backbone.

Exemplary non-steroidal GRAs useful for the practice of the methods disclosed herein having a cyclohexyl-pyrimidine backbone include those described in U.S. Pat. Nos. 8,685,973; 8,906,917; and 9,321,736. In embodiments, the cyclohexyl-pyrimidine GRM is the compound (E)-6-(4-Phenylcyclohexyl)-5-(3-trifluoromethylbenzyl)-1H-pyrimidine-2,4-dione (also termed "miricorilant" and "CORT118335"), which has the structure:

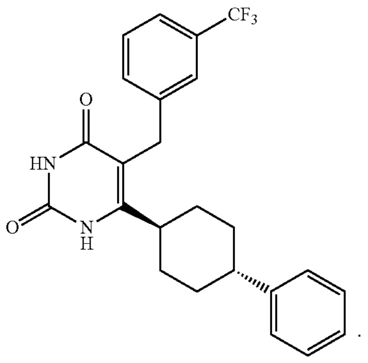 [SMILES: O=c1[nH]c(=O)c(Cc2cccc(C(F)(F)F)c2)c([C@H]2CC[C@H](c3ccccc3)CC2)[nH]1]

Exemplary non-steroidal GRAs useful for the practice of the methods disclosed herein having a fused azadecalin backbone include those described in U.S. Pat. Nos. 7,928,237; and 8,461,172. In embodiments, the fused azadecalin GRM is the compound (R)-4-a-ethoxymethyl-1-(4-fluoro-phenyl)-6-(4-trifluoromethyl-benzenesulfonyl)-4,4a,5,6,7,8-hexahydro-1H,1,2,6-triaza-cyclopenta[b]naphthalene ("CORT108297"), which has the structure:

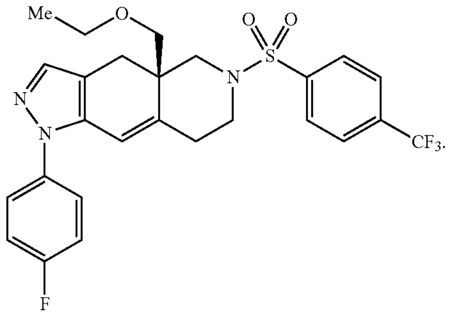 [SMILES: CCOC[C@]12Cc3cnn(-c4ccc(F)cc4)c3C=C1CCN(S(=O)(=O)c1ccc(C(F)(F)F)cc1)C2]

Exemplary non-steroidal GRAs useful for the practice of the methods disclosed herein include heteroaryl-ketone fused azadecalin compounds, such as those described in U.S. Pat. Nos. 8,859,774; 9,273,047; 9,707,223; and 9,956,216, all of which patents are hereby incorporated by reference in their entireties. In embodiments, the heteroaryl-ketone fused azadecalin GRA is the compound (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (Example 18 of U.S. Pat. No. 8,859,774), also known as "relacorilant" and as "CORT125134", which has the following structure:

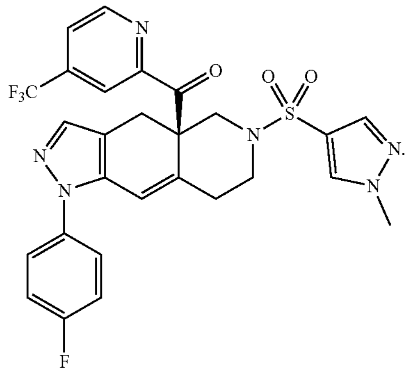 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

In embodiments, the heteroaryl-ketone fused azadecalin GRA is the compound (R)-(1-(4-fluorophenyl)-6-((4-(trifluoromethyl)phenyl)sulfonyl)-4,4a,5,6,-7,8-hexahydro-1H-pyrazolo[3,4-g]isoquinolin-4a-yl)(thiazol-2-yl)methanone (termed "CORT122928"), which has the following structure:

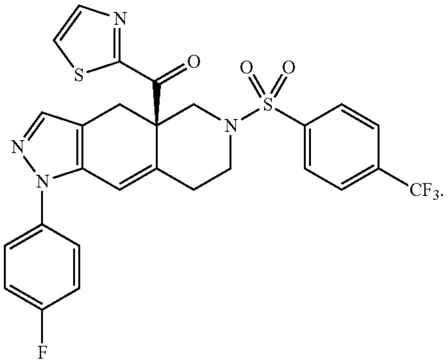 [SMILES: O=C(c1nccs1)[C@]12Cc3cnn(-c4ccc(F)cc4)c3C=C1CCN(S(=O)(=O)c1ccc(C(F)(F)F)cc1)C2]

In embodiments, the heteroaryl-ketone fused azadecalin GRA is the compound (R)-(1-(4-fluorophenyl)-6-((4-(trifluoromethyl)phenyl)sulfonyl)-4, 4a, 5,6,7,8-hexahydro-1-H-pyrazolo P,4-g]isoquinolin-4a-yl) (pyridin-2-yl)methanone (termed "CORT113176"), which has the following structure:

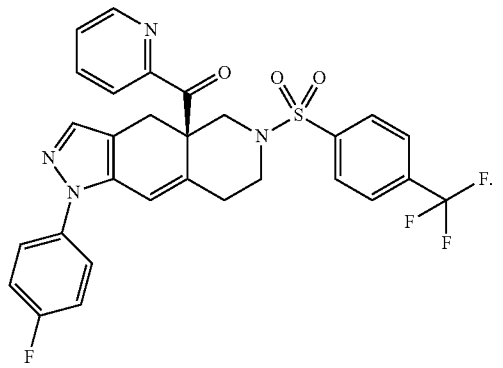 [SMILES: O=C(c1ccccn1)[C@]12Cc3cnn(-c4ccc(F)cc4)c3C=C1CCN(S(=O)(=O)c1ccc(C(F)(F)F)cc1)C2]

Exemplary non-steroidal GRAs useful for the practice of the methods disclosed herein having an octohydro fused azadecalin backbone include those described in U.S. Pat. No. 10,047,082. In embodiments, the octahydro fused azadecalin compound is the compound ((4aR,8aS)-1-(4-fluorophenyl)-6-((2-methyl-2H-1,2,3-triazol-4-yl)sulfonyl)-4,4a, 5,6,7,8,8a,9-octahydro-1H-pyrazolo[3,4-g]isoquinolin-4a-yl)(4-(trifluoromethyl)pyridin-2-yl)methanone (also termed "exicorilant" and "CORT125281") which has the structure:

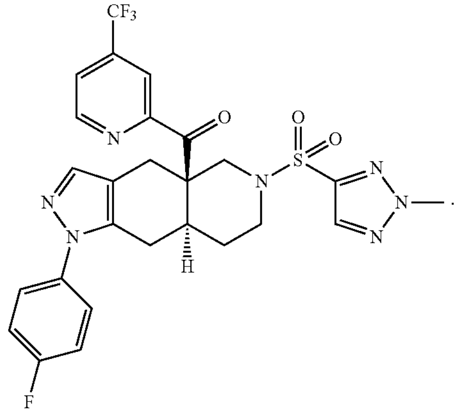 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

Pharmaceutical Compositions of Glucocorticoid Receptor Antagonists

The GRA administered in the practice of the methods disclosed herein can be prepared in any suitable form, including in a wide variety of oral, parenteral and topical dosage forms. Oral preparations of either include tablets, pills, powder, dragees, capsules, liquids, lozenges, cachets, gels, syrups, slurries, suspensions, etc., suitable for ingestion by the patient. The GRA compositions of the present invention can also be administered by injection, that is, intravenously, intramuscularly, intracutaneously, subcutaneously, intraduodenally, or intraperitoneally. Also, the GRA compositions described herein can be administered by inhalation, for example, intranasally. Additionally, the GRA compositions of the present invention can be administered transdermally. The GRA compositions of this invention can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention provides pharmaceutical compositions of a GRA including a pharmaceutically acceptable carrier or excipient and a GRA compound of the present invention.

For preparing pharmaceutical compositions from the GRA compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the GRM or GRA compound for use in the methods disclosed herein.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

Methods of Administration

The GRA compounds or compositions of the present invention can be delivered by any suitable means, including oral, parenteral (e.g., intravenous injection or intramuscular injection) and topical methods. Transdermal administration methods, by a topical route, can be formulated as applicator sticks, solutions, suspensions, emulsions, gels, creams, ointments, pastes, jellies, paints, powders, and aerosols.

The GRA dose may be administered at any time during the day or night. In embodiments of the methods provided herein, a GRA is administered in the morning; and may be administered in the morning prior to the morning meal ("fasted" administration) or may be administered in the morning within about 30 minutes or within about one hour after the patient begins eating the morning meal ("fed" administration, or "with food"). In some embodiments of the methods provided herein, at least one dose of a GRA is administered at about 11 p.m. (e.g., 2300 h) and the level of total or free cortisol (e.g., morning plasma total cortisol, morning serum total cortisol, morning salivary cortisol, serum free cortisol, plasma free cortisol, or urine free cortisol) is measured the following morning at about 8 a.m. or no later than 10 hours after GRA administration.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

GRAs can be administered orally. For example, the GRA can be administered as a pill, a capsule, or liquid formulation as described herein. Alternatively, GRAs can be provided via parenteral administration. For example, the GRA can be administered intravenously (e.g., by injection or infusion). Additional methods of administration of the compounds described herein, and pharmaceutical compositions or formulations thereof, are described herein.

In some embodiments, the GRA is administered in one dose. In other embodiments, the GRA is administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration. The amount will vary according to, for example, the GRA properties.

EXAMPLES

The following examples are offered to illustrate, but not to limit, the claimed invention.

Differential Diagnosis between ACTH-Dependent Cushing's Syndrome and ACTH-Independent Cushing's Syndrome

Example 1

Using ACTH:Cortisol Ratios for Differential Diagnosis

Cushing's syndrome (CS) patients were examined and serum levels of ACTH and cortisol were measured in blood samples obtained from the patients. The serum ACTH and cortisol levels determined prior to administration of glucocorticoid receptor antagonist (GRA) therapy were used to calculate baseline ACTH:cortisol ratios (basal ACTH:cortisol ratios). The baseline ACTH level was less than 25 pg/mL in these patients. The patients then received oral glucocorticoid receptor antagonist (GRA) therapy (either mifepristone or relacorilant, typically daily) for at least six weeks. The serum ACTH and cortisol levels determined after these six weeks of GRA therapy were used to calculate after-GRA ACTH:cortisol ratios. Three patients were treated with relacorilant (100 milligrams (mg) per day, titrated up to 400 mg per day, as tolerated; see Table 1). In the CS patient with a pituitary tumor (pituitary CS) treated with relacorilant the ACTH to cortisol ratio increased (as with the mifepristone cases discussed in the following Table 2) but in the two Cushing's syndrome patients with adrenal tumors (adrenal CS) the ratio decreased following treatment with relacorilant. The results of these clinical measurements in Cushing's syndrome patients administered relacorilant (100 milligrams (mg) per day, titrated up to 400 mg per day, as tolerated) are presented in the Table 1:

TABLE 1

| Tumor Location | | Baseline | Week 6 | Baseline Ratio | Post-Treatment Ratio |
|---|---|---|---|---|---|
| Adrenal CS 1 | ACTH (pg/mL) | 21.9 | 19.8 | 1.35 | 1.16 |
| | Serum Cortisol (μg/dL) | 16.2 | 17.1 | | |
| Adrenal CS 2 | ACTH (pg/ml) | 8.4 | 6 | 0.62 | 0.40 |
| | Serum Cortisol (μg/dL) | 13.6 | 14.9 | | |
| Pituitary CS 1 | ACTH (pg/ml) | 23.9 | 39.8 | 1.15 | 1.39 |
| | Serum Cortisol (μg/dL) | 20.7 | 28.7 | | |

("pg/mL" indicates picograms per milliliter; "μg/dL" indicates micrograms per deciliter)

As shown in Table 1, the ACTH:cortisol ratio decreased following relacorilant treatment in the two CS patients with ACTH-independent Cushing's syndrome (both patients had adrenal gland tumors). In contrast, the ACTH:cortisol ratio increased following relacorilant treatment in the CS patient with ACTH-dependent Cushing's syndrome (this patient had a pituitary tumor). Thus, the change in ACTH:cortisol ratio following GRA (here, relacorilant) administration provides a way to differentially diagnose ACTH-dependent Cushing's syndrome from ACTH-independent Cushing's syndrome.

In another clinical trial, CS patients were treated with mifepristone, and serum levels of ACTH and cortisol were measured in blood samples obtained from the patients at baseline and following GRA treatment. The serum ACTH and cortisol levels determined prior to administration of GRA (mifepristone) therapy were used to calculate basal ACTH and basal cortisol levels, and to calculate baseline ACTH:cortisol ratios (basal ACTH:cortisol ratios). The baseline ACTH level was less than 25 pg/mL in these patients. The patients then received oral mifepristone (typically daily) for at least six weeks. The serum ACTH and cortisol levels determined after these six weeks of mifepristone therapy were used to calculate after-GRA ACTH:cortisol ratios. The results of these clinical measurements in Cushing's syndrome patients administered mifepristone (300 mg per day, titrated up to 900 mg per day, as tolerated) are presented in the Table 2:

TABLE 2

| Patient ID | Basal ACTH (pg/mL) | Basal Serum Cortisol (nmol/L) | Day 14 ACTH (pg/ml) | Day 14 Serum Cortisol (nmol/L) | Week 6 Basal ACTH (pg/ml) | Week 6 Serum Cortisol (nmol/L) | Basal ACTH: Cortisol ratio | Day 14 ACTH: Cortisol ratio | Week 6 ACTH: Cortisol ratio |
|---|---|---|---|---|---|---|---|---|---|
| 01-001 | 7 | 317 | 21 | 900 | 24 | 955 | 0.022 | 0.023 | 0.025 |
| 07-002 | 15 | 494 | 30 | 809 | 49 | 731 | 0.03 | 0.037 | 0.067 |
| 07-007 | 8 | 502 | 22 | 613 | 20 | 654 | 0.016 | 0.036 | 0.031 |
| 08-001 | 16 | 337 | 34 | 486 | 57 | 679 | 0.047 | 0.069 | 0.084 |
| 09-001 | 21 | 632 | 34 | 955 | 52 | 999 | 0.033 | 0.036 | 0.052 |
| 16-002 | 20 | 734 | 53 | 914 | 65 | 1151 | 0.027 | 0.058 | 0.056 |

("pg/mL" indicates picograms per milliliter; "nmol/L" indicates nanomoles per liter)

All patients in Table 2 had confirmed pituitary CS (ACTH dependent CS) and they were all treated with mifepristone. As shown in the Table 2, the ACTH:cortisol ratio increased following mifepristone treatment in these ACTH-dependent Cushing's syndrome patients. Thus, the change in ACTH: cortisol ratio following GRA (here, mifepristone) administration observed in these patients (increase in ACTH-dependent Cushing's patients following GRA therapy) is consistent with the observations shown in Table 1 and thus the present results provide a way to differentially diagnose ACTH-dependent Cushing's syndrome from ACTH-independent Cushing's syndrome. In addition, these data show that an increase in ACTH above 25 pg/mL following GRA therapy can serve as a separate, or additional, criterion for identifying ACTH-dependent Cushing's syndrome. Thus, differential diagnosis can be done either with the ACTH: cortisol ratio, or with the increase above the 25 pg/mL threshold, or both.

Example 2

Both ACTH and Cortisol Rise Following GRA Administration

A patient is examined and is determined to suffer from Cushing's syndrome. An initial cortisol level and an initial ACTH level is determined from one or more blood samples obtained from the patient. The initial ACTH level is less than 25 pg/mL.

The patient is administered 600 milligrams (mg) per day of the glucocorticoid receptor antagonist (GRA) mifepristone. A further ACTH level and a further cortisol level is determined from one or more blood samples obtained from the patient after administration of the mifepristone. The further ACTH level is greater than the initial ACTH level. The further cortisol level is also greater than the initial cortisol level.

Based on the rise in ACTH level and the rise in cortisol level, the patient is determined to suffer from ACTH-Dependent Cushing's syndrome.

Example 3

ACTH, but not Cortisol, Rises Following GRA Administration

A patient is examined and is determined to suffer from Cushing's syndrome. An initial cortisol level and an initial ACTH level is determined from one or more blood samples obtained from the patient. The initial ACTH level is less than 25 pg/mL.

The patient is administered 600 milligrams (mg) per day of the glucocorticoid receptor antagonist (GRA) mifepristone. A further ACTH level and a further cortisol level is determined from one or more blood samples obtained from the patient after administration of the mifepristone. The further ACTH level is greater than the initial ACTH level. The further cortisol level is not greater than the initial cortisol level.

Based on the rise in ACTH level, the patient is determined to suffer from ACTH-Dependent Cushing's syndrome.

Example 4

Cortisol, but not ACTH, Rises Following GRA Administration

A patient is examined and is determined to suffer from Cushing's syndrome. An initial cortisol level and an initial ACTH level is determined from one or more blood samples obtained from the patient. The initial ACTH level is less than 25 pg/mL.

The patient is administered 600 milligrams (mg) per day of the glucocorticoid receptor antagonist (GRA) mifepristone. A further ACTH level and a further cortisol level is determined from one or more blood samples obtained from the patient after administration of the mifepristone. The further ACTH level is not greater than the initial ACTH level. The further cortisol level is greater than the initial cortisol level.

Based on the rise in cortisol level, the patient is determined to suffer from ACTH-Dependent Cushing's syndrome.

Example 5

Neither ACTH Nor Cortisol Rises Following GRA Administration

A patient is examined and is determined to suffer from Cushing's syndrome. An initial cortisol level and an initial ACTH level is determined from one or more blood samples obtained from the patient. The initial ACTH level is less than 25 pg/mL.

The patient is administered 600 milligrams (mg) per day of the glucocorticoid receptor antagonist (GRA) mifepristone. A further ACTH level and a further cortisol level is determined from one or more blood samples obtained from the patient after administration of the mifepristone. The further ACTH level is not greater than the initial ACTH level. The further cortisol level is not greater than the initial cortisol level.

Based on the lack of rise in either the ACTH level or in the cortisol level, the patient is determined to suffer from ACTH-Independent Cushing's syndrome.

Example 6

Both ACTH and an Adrenal Hormone or Pre-Hormone Rise Following GRA Administration A patient is examined and is determined to suffer from Cushing's syndrome. An initial ACTH level, and an initial adrenal hormone or pre-hormone level is determined from one or more blood samples obtained from the patient. The adrenal hormone or pre-hormone is selected from 17α-hydroxy pregnenolone, 17α-hydroxy progesterone, 11-deoxycortisol, pregnenolone, progesterone, 11-deoxycorticosterone, corticosterone, 18-hydroxycorticosterone, aldosterone, dehydroepiandrosterone (androstenolone, DHEA), dehydroepiandrosterone sulfate (DHEA-S), and androstenedione. The initial ACTH level is less than 25 pg/mL.

The patient is administered 600 milligrams (mg) per day of the glucocorticoid receptor antagonist (GRA) mifepristone. A further ACTH level and a further adrenal hormone or pre-hormone level is determined from one or more blood samples obtained from the patient after administration of the mifepristone. The further ACTH level is greater than the initial ACTH level. The further adrenal hormone or pre-hormone level is also greater than the initial adrenal hormone or pre-hormone level.

Based on the rise in ACTH level and the rise in adrenal hormone or pre-hormone level, the patient is determined to suffer from ACTH-Dependent Cushing's syndrome.

Example 7

ACTH, but not an Adrenal Hormone or Pre-Hormone, Rises Following GRA Administration A patient is examined and is determined to suffer from Cushing's syndrome. An initial ACTH level, and an initial adrenal hormone or pre-hormone level is determined from one or more blood samples obtained from the patient. The adrenal hormone or pre-hormone is selected from 17α-hydroxy pregnenolone, 17α-hydroxy progesterone, 11-deoxycortisol, pregnenolone, progesterone, 11-deoxycorticosterone, corticosterone, 18-hydroxycorticosterone, aldosterone, dehydroepiandrosterone (androstenolone, DHEA), dehydroepiandrosterone sulfate (DHEA-S), and androstenedione. The initial ACTH level is less than 25 pg/mL.

The patient is administered 600 milligrams (mg) per day of the glucocorticoid receptor antagonist (GRA) mifepristone. A further ACTH level and a further adrenal hormone or pre-hormone level is determined from one or more blood samples obtained from the patient after administration of the mifepristone. The further ACTH level is greater than the initial ACTH level. The further adrenal hormone or pre-hormone level is not greater than the initial adrenal hormone or pre-hormone level.

Based on the rise in ACTH level, the patient is determined to suffer from ACTH-Dependent Cushing's syndrome.

Example 8

An Adrenal Hormone or Pre-Hormone, but not ACTH, Rises Following GRA Administration A patient is examined and is determined to suffer from Cushing's syndrome. An initial ACTH level, and an initial adrenal hormone or pre-hormone level is determined from one or more blood samples obtained from the patient. The adrenal hormone or pre-hormone is selected from 17α-hydroxy pregnenolone, 17α-hydroxy progesterone, 11-deoxycortisol, pregnenolone, progesterone, 11-deoxycorticosterone, corticosterone, 18-hydroxycorticosterone, aldosterone, dehydroepiandrosterone (androstenolone, DHEA), dehydroepiandrosterone sulfate (DHEA-S), and androstenedione. The initial ACTH level is less than 25 pg/mL.

The patient is administered 600 milligrams (mg) per day of the glucocorticoid receptor antagonist (GRA) mifepristone. A further ACTH level and a further adrenal hormone or pre-hormone level is determined from one or more blood samples obtained from the patient after administration of the mifepristone. The further ACTH level is not greater than the initial ACTH level. The further adrenal hormone or pre-hormone level is greater than the initial adrenal hormone or pre-hormone level.

Based on the rise in adrenal hormone or pre-hormone level, the patient is determined to suffer from ACTH-Dependent Cushing's syndrome.

Example 9

Neither ACTH Nor an Adrenal Hormone or Pre-Hormone Rises Following GRA Administration A patient is examined and is determined to suffer from Cushing's syndrome. An initial ACTH level, and an initial adrenal hormone or pre-hormone level is determined from one or more blood samples obtained from the patient. The adrenal hormone or pre-hormone is selected from 17α-hydroxy pregnenolone, 17α-hydroxy progesterone, 11-deoxycortisol, pregnenolone, progesterone, 11-deoxycorticosterone, corticosterone, 18-hydroxycorticosterone, aldosterone, dehydroepiandrosterone (androstenolone, DHEA), dehydroepiandrosterone sulfate (DHEA-S), and androstenedione. The initial ACTH level is less than 25 pg/mL.

The patient is administered 600 milligrams (mg) per day of the glucocorticoid receptor antagonist (GRA) mifepristone. A further ACTH level and a further adrenal hormone or pre-hormone level is determined from one or more blood samples obtained from the patient after administration of the mifepristone. The further ACTH level is not greater than the initial ACTH level. The further adrenal hormone or pre-hormone level is not greater than the initial adrenal hormone or pre-hormone level.

Based on the lack of rise in either the ACTH level or in the adrenal hormone or pre-hormone level, the patient is determined to suffer from ACTH-Independent Cushing's syndrome.

It will be understood that the exemplary dose of 600 mg/day mifepristone can be varied in the methods disclosed herein. For example, a dose of 300 mg/day mifepristone may be used in the methods disclosed herein. For further example, a dose of 900 mg/day mifepristone may be used in the methods disclosed herein. For yet further example, a dose or 1200 mg/day mifepristone may be used in the methods disclosed herein. Based on a rise in either the ACTH level or in the cortisol level, a patient receiving 300 mg/day, or 900 mg/day, or 1200 mg/day of mifepristone is determined to suffer from ACTH-dependent Cushing's syndrome. Based on a lack of rise in either the ACTH level or in the cortisol level, a patient receiving 300 mg/day, or 900 mg/day, or 1200 mg/day of mifepristone is determined to suffer from ACTH-Independent Cushing's syndrome.

It will be further understood that the multiple measurements may be used in methods disclosed herein, including measurements of ACTH, cortisol, and an adrenal hormone or pre-hormone; and including measurements of ACTH, cortisol, and multiple adrenal hormones, pre-hormone, and combinations thereof.

Although the foregoing invention has been described in some detail by way of illustration and example for purposes of clarity of understanding, one of skill in the art will appreciate that certain changes and modifications may be practiced within the scope of the appended claims. In addition, all patents, patent publications, and references provided herein are hereby incorporated by reference herein in their entireties to the same extent as if each reference was individually incorporated by reference.

We claim:

1. A method of treating Cushing's syndrome in a patient and differentially diagnosing between adrenocorticotropin hormone (ACTH)-Dependent Cushing's syndrome and ACTH-Independent Cushing's syndrome during the treatment, the method comprising:

(a) selecting a patient having Cushing's syndrome, having a basal level of plasma or serum cortisol, and having a basal level of plasma or serum ACTH that is between about 5 picograms per milliliter (pg/mL) and about 25 μg/mL;

(b) administering to the patient for at least 6 weeks a daily dose of a glucocorticoid receptor antagonist (GRA) selected from: a dose of mifepristone of between about 300 milligrams (mg) and about 1200 mg, and a dose of between about 25 mg and about 550 mg of a GRA compound selected from the group of GRA compounds having a non-steroidal backbone consisting of a GRA compound having a cyclohexyl pyrimidine backbone, a GRA compound having a fused azadecalin backbone, a GRA compound having a heteroaryl-ketone fused azadecalin backbone, and a GRA compound having an octahydro fused azadecalin backbone, wherein said GRA administration comprises a treatment of said Cushing's syndrome;

(c) measuring a level of ACTH or of cortisol in an after-GRA plasma or serum sample obtained from the patient after said at least six weeks of daily GRA administration, wherein said after-GRA sample is a plasma or serum sample corresponding to the type of sample from which the basal level was determined; and (d) determining that the patient has ACTH-Dependent Cushing's syndrome if, after said at least six weeks of daily GRA administration, one or both of the patient's ACTH levels or the patient's cortisol levels, as measured in said plasma or serum sample, are increased by at least 10% in the plasma or serum sample as compared to their respective basal levels; or (e) determining that the patient has ACTH-Independent Cushing's syndrome if, after said at least six weeks of daily GRA administration, neither the patient's ACTH level nor the patient's cortisol level are increased as compared to their respective basal levels, whereby Cushing's syndrome is further treated with said GRA administration or with surgical treatment to remove a tumor depending on the differential diagnosis between a) ACTH-Dependent Cushing's syndrome and between b) ACTH-Independent Cushing's syndrome in the patient.

2. The method of claim 1, wherein the patient is identified as having ACTH-Dependent Cushing's syndrome and then undergoes surgery to remove an adrenocorticotrophic hormone (ACTH) secreting tumor.

3. The method of claim 2, wherein the tumor is a pituitary ACTH secreting tumor.

4. The method of claim 2, wherein the tumor is an ectopic ACTH secreting tumor.

5. The method of claim 1, wherein the GRA is administered orally.

6. The method of claim 1, wherein the glucocorticoid receptor antagonist is mifepristone.

7. The method of claim 1, wherein the glucocorticoid receptor antagonist (GRA) comprises a GRA compound having a non-steroidal backbone selected from a cyclohexyl pyrimidine backbone, a fused azadecalin backbone, a heteroaryl-ketone fused azadecalin backbone, and an octahydro fused azadecalin backbone.

8. The method of claim 7, wherein the glucocorticoid receptor antagonist is selected from the cyclohexyl pyrimidine compound (E)-6-(4-Phenylcyclohexyl)-5-(3-trifluoromethylbenzyl)-1H-pyrimidine-2,4-dione, which has the structure:

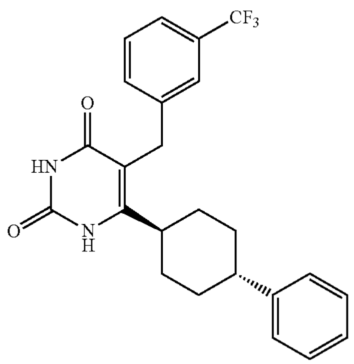
;

the fused azadecalin compound (R)-4-a-ethoxymethyl-1-(4-fluoro-phenyl)-6-(4-trifluoromethyl-benzenesulfonyl)-4,4a,5,6,7,8-hexahydro-1H,1,2,6-triaza-cyclopenta[b]naphthalene, which has the structure:

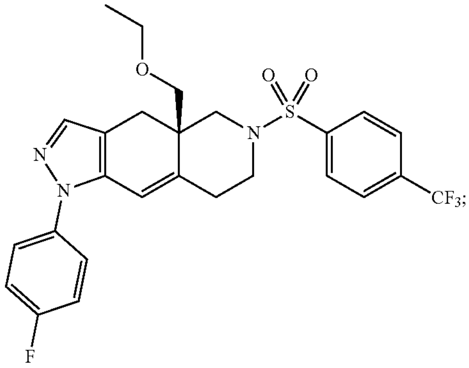 [SMILES: CCOC[C@]12Cc3cnn(-c4ccc(F)cc4)c3C=C1CCN(S(=O)(=O)c1ccc(C(F)(F)F)cc1)C2]

the heteroaryl-ketone fused azadecalin compound (R)-(1-(4-fluorophenyl)-6-((1-methyl-1H-pyrazol-4-yl) sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

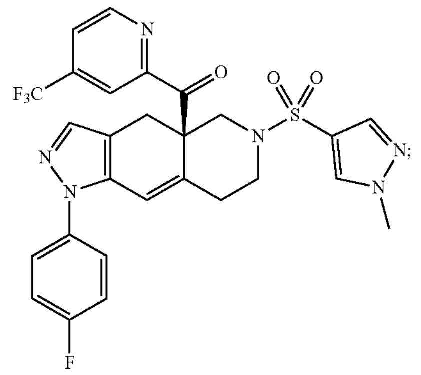 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

the heteroaryl-ketone fused azadecalin compound (R)-(1-(4-fluorophenyl)-6-((4-(trifluoromethyl)phenyl)sulfonyl)-4,4a,5,6,-7,8-hexahydro-1H-pyrazolo[3,4-g]isoquinolin-4a-yl) (thiazol-2-yl)methanone, which has the following structure:

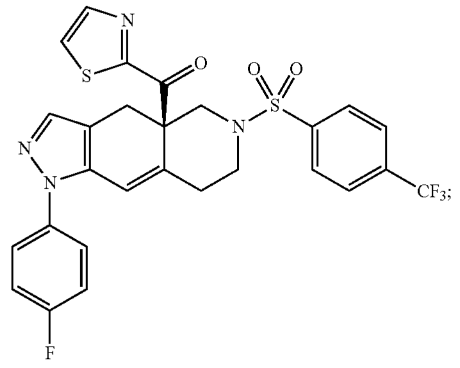 [SMILES: O=C(c1nccs1)[C@]12Cc3cnn(-c4ccc(F)cc4)c3C=C1CCN(S(=O)(=O)c1ccc(C(F)(F)F)cc1)C2]

the heteroaryl-ketone fused azadecalin compound (R)-(1-(4-fluorophenyl)-6-((4-(trifluoromethyl)phenyl) sulfonyl)-4, 4a, 5,6,7,8-hexahydro-1-H-pyrazolo P,4-g]isoquinolin-4a-yl) (pyridin-2-yl)methanone, which has the following structure:

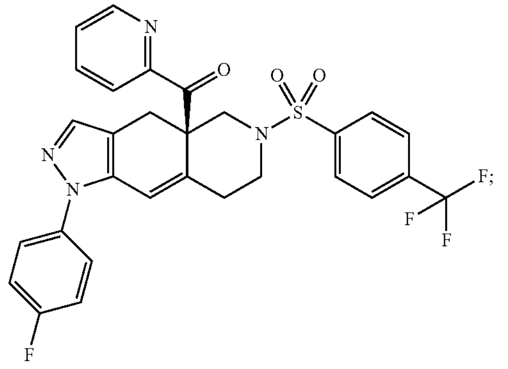 [SMILES: O=C(c1ccccn1)[C@]12Cc3cnn(-c4ccc(F)cc4)c3C=C1CCN(S(=O)(=O)c1ccc(C(F)(F)F)cc1)C2]

and the octahydro fused azadecalin compound ((4aR,8aS)-1-(4-fluorophenyl)-6-((2-methyl-2H-1,2,3-triazol-4-yl) sulfonyl)-4,4a,5,6,7,8,8a,9-octahydro-1H-pyrazolo[3,4-g] isoquinolin-4a-yl) (4-(trifluoromethyl)pyridin-2-yl)methanone, which has the structure:

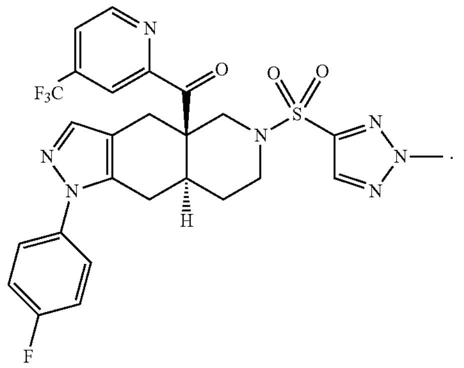 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

9. A method of treating Cushing's syndrome in a patient and differentially diagnosing between adrenocorticotropin hormone (ACTH)-Dependent Cushing's syndrome and ACTH-Independent Cushing's syndrome during the treatment, the method comprising:

(a) selecting a patient having Cushing's syndrome, having a basal level of plasma or serum cortisol, and having a basal level of plasma or a basal level of serum ACTH having a numerical value that is between about 5 picograms per milliliter (pg/mL) and about 25 µg/mL;

(b) determining a basal ACTH:cortisol ratio by dividing the numerical value of the plasma or serum basal ACTH level by a numerical value of the corresponding plasma or serum basal cortisol level to provide said basal ACTH:cortisol ratio;

(c) administering to the patient for at least 6 weeks a daily dose of a glucocorticoid receptor antagonist (GRA) selected from: a dose of mifepristone of between about 300 milligrams (mg) and about 1200 mg, and a dose of between about 25 mg and about 550 mg of a GRA compound selected from the group of GRA compounds having a non-steroidal backbone consisting of a GRA compound having a cyclohexyl pyrimidine backbone, a GRA compound having a fused azadecalin backbone, a GRA compound having a heteroaryl-ketone fused azadecalin backbone, and a GRA compound having an octahydro fused azadecalin backbone, wherein said GRA administration comprises a treatment of said Cushing's syndrome;

(d) measuring a level of ACTH to determine a numerical value of the ACTH level and a level of cortisol to determine a numerical value of the cortisol level in an after-GRA plasma sample or a serum sample obtained from the patient after said 6 weeks of daily GRA administration, wherein said after-GRA sample is a plasma or serum sample corresponding to the type of sample from which the basal level was determined;

(e) determining an after-GRA ACTH:cortisol ratio by dividing the numerical value of the plasma or serum ACTH level measured after GRA administration by the numerical value of the corresponding plasma or serum cortisol level measured after said at least six weeks of daily GRA administration to provide said after-GRA ACTH:cortisol ratio;

and differentially diagnosing between adrenocorticotropin hormone (ACTH)-Dependent Cushing's syndrome and ACTH-Independent Cushing's syndrome by comparing said basal ACTH:cortisol ratio to said after-GRA ACTH:cortisol ratio, wherein if the basal ACTH:cortisol ratio is greater than the after-GRA ACTH:cortisol ratio by at least about 10% of the basal ACTH:cortisol ratio, then the patient is diagnosed with ACTH-independent Cushing's syndrome; and if the basal ACTH:cortisol ratio is smaller than the after-GRA ACTH:cortisol ratio by at least about 10% of the basal ACTH:cortisol ratio, then the patient is diagnosed with ACTH-dependent Cushing's syndrome, whereby Cushing's syndrome is further treated with said GRA administration or with surgical treatment to remove a tumor depending on the differential diagnosis between a) ACTH-Dependent Cushing's syndrome and between b) ACTH-Independent Cushing's syndrome in the patient.

10. The method of claim 9, further comprising comparing the basal ACTH:cortisol ratio determined before GRA treatment with the after-GRA ACTH:cortisol ratio determined after GRA treatment to determine a change in ACTH:cortisol ratio, wherein the change in ACTH:cortisol ratio from before GRA treatment to after GRA treatment is at least about 15% of the basal ACTH:cortisol ratio.

11. The method of claim 9, further comprising comparing the basal ACTH:cortisol ratio determined before GRA treatment with the after-GRA ACTH:cortisol ratio determined after GRA treatment to determine a change in ACTH:cortisol ratio, wherein the change in ACTH:cortisol ratio from before GRA treatment to after GRA treatment is at least about 20% of the basal ACTH:cortisol ratio.

12. The method of claim 9, further comprising comparing the basal ACTH:cortisol ratio determined before GRA treatment with the after-GRA ACTH:cortisol ratio determined after GRA treatment to determine a change in ACTH:cortisol ratio, wherein the change in ACTH:cortisol ratio from before GRA treatment to after GRA treatment is greater than about 25% of the basal ACTH:cortisol ratio.

13. The method of claim 9, wherein the GRA is administered orally.

14. The method of claim 9, wherein the glucocorticoid receptor antagonist is mifepristone.

15. The method of claim 9, wherein the glucocorticoid receptor antagonist (GRA) comprises a GRA compound having a non-steroidal backbone selected from a GRA compound having a cyclohexyl pyrimidine backbone, a GRA compound having a fused azadecalin backbone, a GRA compound having a heteroaryl-ketone fused azadecalin backbone, and a GRA compound having an octahydro fused azadecalin backbone.

16. The method of claim 15, wherein the glucocorticoid receptor antagonist is selected from the cyclohexyl pyrimidine compound (E)-6-(4-Phenylcyclohexyl)-5-(3-trifluoromethylbenzyl)-1H-pyrimidine-2,4-dione, which has the structure:

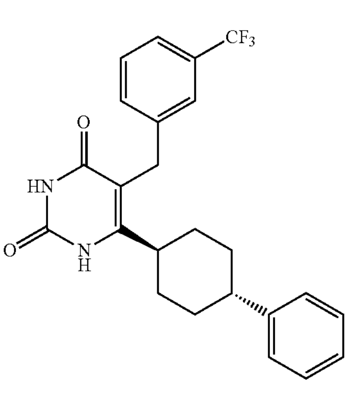

;

the fused azadecalin compound (R)-4-a-ethoxymethyl-1-(4-fluoro-phenyl)-6-(4-trifluoromethyl-benzenesulfonyl)-4,4a,5,6,7,8-hexahydro-1H,1,2,6-triaza-cyclopenta[b]naphthalene, which has the structure:

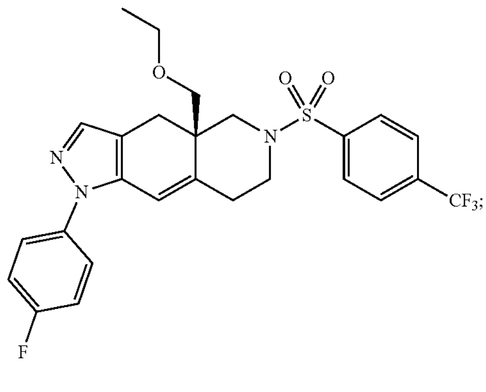 [SMILES: CCOC[C@]12Cc3cnn(-c4ccc(F)cc4)c3C=C1CCN(S(=O)(=O)c1ccc(C(F)(F)F)cc1)C2]

;

the heteroaryl-ketone fused azadecalin compound (R)-(1-(4-fluorophenyl)-6-((1-methyl-1H-pyrazol-4-yl) sulfonyl)-4,4a,5,6,7,8-hexahydro-1H-pyrazolo[3,4-g]isoquinolin-4a-yl) (4-(trifluoromethyl)pyridin-2-yl)methanone, which has the following structure:

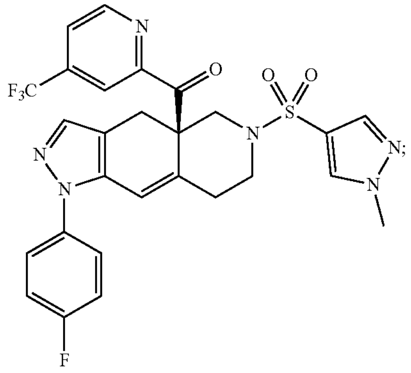 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

;

the heteroaryl-ketone fused azadecalin compound (R)-(1-(4-fluorophenyl)-6-((4-(trifluoromethyl)phenyl)sulfonyl)-4,4a,5,6,-7,8-hexahydro-1H-pyrazolo[3,4-g]isoquinolin-4a-yl) (thiazol-2-yl)methanone, which has the following structure:

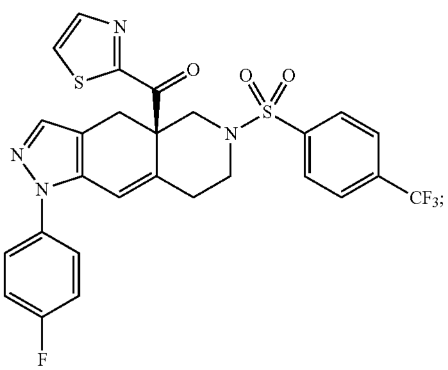 [SMILES: O=C(c1nccs1)[C@]12Cc3cnn(-c4ccc(F)cc4)c3C=C1CCN(S(=O)(=O)c1ccc(C(F)(F)F)cc1)C2]

;

the heteroaryl-ketone fused azadecalin compound (R)-(1-(4-fluorophenyl)-6-((4-(trifluoromethyl)phenyl)sulfonyl)-4, 4a, 5,6,7,8-hexahydro-1-H-pyrazolo P,4-g]isoquinolin-4a-yl) (pyridin-2-yl)methanone, which has the following structure:
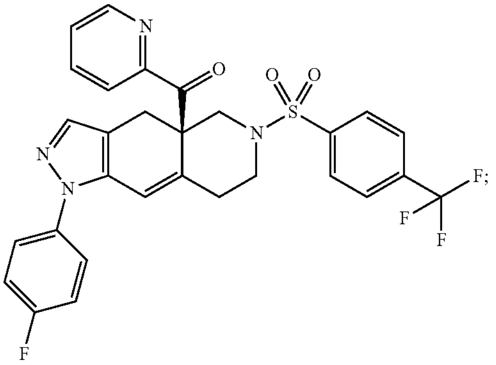 [SMILES: O=C(c1ccccn1)[C@]12Cc3cnn(-c4ccc(F)cc4)c3C=C1CCN(S(=O)(=O)c1ccc(C(F)(F)F)cc1)C2]
and the octahydro fused azadecalin compound ((4aR,8aS)-1-(4-fluorophenyl)-6-((2-methyl-2H-1,2,3-triazol-4-yl) sulfonyl)-4,4a,5,6,7,8,8a,9-octahydro-1H-pyrazolo[3,4-g] isoquinolin-4a-yl) (4-(trifluoromethyl)pyridin-2-yl)methanone, which has the structure:
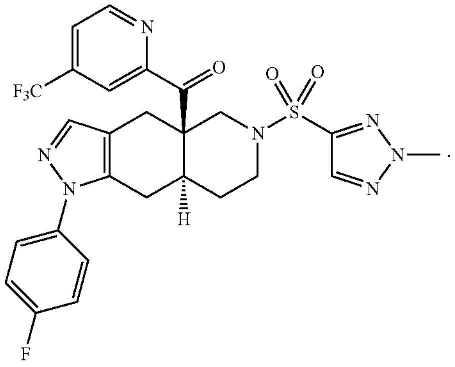 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]
* * * * *